United States Patent
Landauer et al.

(10) Patent No.: US 8,349,888 B2
(45) Date of Patent: *Jan. 8, 2013

(54) PHYTOESTROGENIC ISOFLAVONE COMPOSITIONS, THEIR PREPARATION AND USE THEREOF FOR PROTECTION AGAINST AND TREATMENT OF RADIATION INJURY

(75) Inventors: Michael R. Landauer, Bethesda, MD (US); Thomas Michael Seed, Bethesda, MD (US); Venkataraman Srinivasan, Germantown, MD (US); Alla Shapiro, Rockville, MD (US); Chris H. Takimoto, Boerne, TX (US)

(73) Assignees: The United States of America as represented by the Secretary Department of Health and Human Services, Washington, DC (US); Henry M. Jackson Foundation for the Advancement of Military Medicine, Rockville, MD (US)

( * ) Notice: Subject to any disclaimer, the term of this patent is extended or adjusted under 35 U.S.C. 154(b) by 338 days.

This patent is subject to a terminal disclaimer.

(21) Appl. No.: 12/696,285

(22) Filed: Jan. 29, 2010

(65) Prior Publication Data

US 2010/0197779 A1    Aug. 5, 2010

Related U.S. Application Data

(63) Continuation of application No. 10/297,978, filed as application No. PCT/US01/19089 on Jun. 12, 2001, now Pat. No. 7,655,694.

(60) Provisional application No. 60/223,734, filed on Aug. 8, 2000, provisional application No. 60/211,375, filed on Jun. 14, 2000.

(51) Int. Cl.
*A61K 31/35* (2006.01)
*A01N 43/16* (2006.01)

(52) U.S. Cl. ...................................... 514/456; 514/460
(58) Field of Classification Search .................. 514/456, 514/460
See application file for complete search history.

(56) References Cited

U.S. PATENT DOCUMENTS

| 5,824,702 | A | 10/1998 | Wei |
| 5,994,409 | A | 11/1999 | Stogniew et al. |
| 6,071,956 | A | 6/2000 | Slepian et al. |
| 6,399,655 | B1 | 6/2002 | De Juan, Jr. |
| 6,426,362 | B1 | 7/2002 | Miller et al. |
| 6,524,832 | B1 | 2/2003 | Kufe et al. |
| 6,544,566 | B1 | 4/2003 | Waggle et al. |
| 7,033,606 | B1 | 4/2006 | Besse et al. |

FOREIGN PATENT DOCUMENTS

| CA | 2337152 A1 | 2/2000 |
| EP | 0943245 A1 | 9/1999 |
| JP | 11-292898 | 10/1999 |
| JP | 2002-521321 | 7/2002 |
| WO | WO 98/08503 | 3/1998 |
| WO | WO 00/04878 | 2/2000 |
| WO | WO 01/95901 A1 | 12/2001 |

OTHER PUBLICATIONS

Agarwal et al., "Radioprotective Property of Flavonoids in Mice", Toxicon, 1981, 19(2), 201-204.
Kemertelidze et al., "Structure-Function Analysis of the Radioprotective and Antioxidant Activity of Flavonoids", Chemistry of Natural Compounds, (Translation of Khimiya Prirodnykh Soedinenii), Jan. 2000, 36(1), 54-59.
Shimoi et al., "Radioprotective Effects of Antioxidative Plant Flavonoids in Mice", Mutation Ressearch—Fundamental and Molecular Mechanisms of Mutagenesis, 1996, 350(1), 153-161.
Akimoto et al., Int J Rad Oncology, Biol. Phys., 2001, 50(1), 195-201.
Beinvenu, P., et al., "Antioxidant effects in radioprotection," Antioxidants in Therapy and Preventive Medicine., 1990, 264, 291-300.
Booth et al., British J of Cancer, 1999, 80(10), 1550-1557.
Bottollier-Depois, J.-F., et al., "Assessing exposure to cosmic radiation during long-haul flight," Radiat. Res., 2000, 153, 526-532.
Casarett, Radiation Biology, 1968, Ch. 10, 1-7.
Coughenour, L.L., et al., "A new device for the rapid measurement of impaired motor function in mice," Pharmacol. Biochem. & Behav., 1977, 6, 351-353.
Dauer and Coon, Flavonoids on Xray Mortality, p. 702-707, 1952.
Devi et al., The British J of Radiology, 1998, 782-784.
Devi, et al., "In vivo radioprotection by ocimum flavonoids: survival of mice," Radiat, Res., 1999, 151(1), 74-78.
Emerit, I., et al., "Oxidative stress-related clastogenic factors in plasma for Chernobyl liquidators: protective effects of antioxidant plant phenols, vitamins an oligoelements," Mutat. Res., 1997, 377(2), 239-246.
Fotsis et al., J Nutr., 1995, 790S-797S.
Guidance for Industry (FDA), Jul. 2005, 1-27.
Hakov'a et al., J. Pharm Pharmacol., Oct. 1993, 45(10), 910-912.
Haley and Mann, Ineffectiveness of flavenoids in Radiation, p. 665-667, 1952.
Hargreaves et al., The J of Clinical Endocrinology and Metabolism, 1999, 84(11), 4017-4023.
Hilmann et al., Clinical Cancer Research, 2001, 7, 382-390.
Kelloff, G.J., et al., "Progress in cancer chemoprevention: development of diet-derived chemopreventive agents," J. Nutr., 2000, 130, 467S-471S.
Kennedy, C.W., et al., "Effects of the bowman-birk protease inhibitor on survival of fibroblasts and cancer cells exposed to radiation and cis-platinum," Nutr. Canc., 1996, 26, 209-217.
Kim, H., et al., "Mechanisms of action of the soy isoflavone genistein: emerging role for its effects via transforming growth factor β signaling pathways," Am. J. Clin. Nutr., 1998, 68, 1418S-1425S.
Kuo, S.-M., "Dietary flavonoid and cancer prevention: evidence and potential mechanism," Organogenesis, 1997, 8(1), 47-69.

(Continued)

*Primary Examiner* — Sreeni Padmanabhan
*Assistant Examiner* — Uma Ramachandran
(74) *Attorney, Agent, or Firm* — Woodcock Washburn LLP

(57) ABSTRACT

The present invention provides compositions and methods for the prophylactic and therapeutic treatment of animals, including humans from radiation injury. In particular, the present invention provides methods and compositions comprising the isoflavone genistein (4',5,7-trihydroxyflavone) or phytoestrogenic isoflavonoids.

20 Claims, 24 Drawing Sheets

OTHER PUBLICATIONS

Landauer, M.R., "Genistein treatment protects mice from ionizing radiation injury," J. of Applied Toxicology, 2003, 23, 379-385.

Landauer, M.R., et al., "Synthetic trehalose dicorynomycolate (S-TDCM): behavioral effects and radioprotection," J. Radiat. Res., 1997, 38, 45-54.

Landauer, R., et al., "Protection from lethal irradiation by genistein," International J. of Toxicology, 2000, 19(6), p. 37.

Li et al., "Soybean isoflavones reduce experimental metastasis in mice," J of Nutrition, 1999, 129, 1075-1078.

Liu, R., et al., "Analysis of mechanisms involved in the prevention of γ irradiation-induced apoptosis by hGM-CSF," Oncogene, 2000, 19, 571-579.

MacPhail, P.C., "Motor activity and screening for neurotoxicity," J. Am. Coll. of Toxicol., 1989, 8(1), 117-125.

McPherson, C.W., "Reduction of *Pseudomonas aeruginosa* and coliform bacteria in mouse drinking water following treatment with hydrochloric acid or chlorine," Lab. Animal Care, 1963, 13, 737-744.

Messina, M.J., "Legumes and soybeans: overview of their nutritional profiles and health effects," Am. J. Clin. Nutr., 1999, 70(Suppl.), 439S-450S.

Meyer, O.A., et al., "A method for the routine assessment of fore- and hind-limb grip strength of rats and mice," Neurobehav. Toxicol., 1979, 1, 233-236.

Miernicki, M., et al., "Radioprotective efficacy of 17β-estradiol in mice," Soc. Neurosci. Abstr., 1990, 16, Abstract No. 433.19, p. 1054.

Papazisis et al., Cancer Letters, 2000, 160, 107-113.

Parsons, J.L., et al., "interplanetary crew dose rates for the Aug. 1972 solar particle event," Radiat. Res., 2000, 153, 729-733.

Patt, H.M., et al., "Influence of estrogens on the acute x-irradiation syndrome," Amer. J. Physiol., 1949, 159, 269-280.

Ravindranath et al., Adv in Exptl Medicine and Biology, 2004, 546, 121-165.

Shimoi, et al., "Radioprotective effect of antioxidative flavonoids in gamma-ray irradiated mice," Carcinogenesis, 1994, 15(11), 2669-2672.

Takimoto, C.H., "Phase I pharmacokinetic and pharmacodynamic analysis of unconjugated soy isoflavones administered to individuals with cancer," Cancer, Epidemiology, Biomarkers & Prevention, 2003, 121213-1221.

Traganos et al., Cancer Research, 1992 52, 6200-6208.

Uckun, F.M., et al., "In vivo toxicity, pharmacokinetics, and anticancer activity of genistein linked to recombinant human epidermal growth factor," Clin. Canc. Res., 1998, 4, 1125-1134.

Van Rijn, J., et al., "Flavonoids as enhancers of X-ray-induced cell damage in hepatoma cells," Clin. Canc. Res., 1997, 3, 1775-1779.

Wei, H., et al., "Antioxidant and antipromotional effects of the soybean isoflavone genistein $_{(43844)}$," Proc. Soc. Exp. Biol. Med., 1995, 208, 124-130.

Weiss et al., Annals of the NY Academy of Sciences, Jan. 2000, 899, 44-60.

Weiss, J.F., et al., "Radioprotection by antioxidants," Ann. NY Acad. Sci., 2000, 899, 44-60.

Iberall, A.S., "The problem of low-dose radiation toxicity," Am. J. Physiol. Regulatory Integrative Comp. Physiol., 1983, 244, 7-13.

Koko Gyi and Stanley Marcus, "Effects of Acute and Chronic Exposure to X-Radiation on Phagocytic Activity," From the Department of Bacteriology, University of Utah College of Medicine, Salt Lake City, Utah, Apr. 15, 1957, 312-318.

Radiation Injury: Accidents & Injuries. Merck Manual Home Edition, Feb. 2003, 5 pages, Accessed via the Internet on Mar. 3, 2009.

Cassarett, "Late Effects of Radiation" in Radiation Biology, 1968, Ch. 12, pp. 266-283.

Merck Manual Online Medical Library, http://www.merck.com/mmhe/sec24/ch292/ch292a.html, 2 pages, 2009.

CDC Fact Sheet, May 20, 2005, 2 pages.

Emerit et al., Radiat Res., Nov. 1995, 144(2), 198-205 [abstract only].

Hall, E.J., Radiobiology for the Radiobiologist, $4^{th}$ ed., 1994, Ch. 18, pp. 311-316, J.B. Lippincott Company, Philadelphia.

Genistein

PHYTOESTROGENIC ISOFLAVONE COMPOSITIONS, THEIR PREPARATION AND USE THEREOF FOR PROTECTION AGAINST AND TREATMENT OF RADIATION INJURY

CROSS REFERENCE TO RELATED APPLICATIONS

This application is a continuation of U.S. patent application Ser. No. 10/297,978, filed Jun. 10, 2004, which is the National Stage of International Application No. PCT/US01/19089 filed Jun. 12, 2001 which claims benefit to U.S. Provisional Application No. 60/223,734 filed Aug. 8, 2000 and U.S. Provisional Application No. 60/211,375 filed Jun. 14, 2000. Each of these applications are incorporated herein by reference in their entirety.

FIELD OF THE INVENTION

The present invention provides compositions and methods for the prophylactic and therapeutic treatment of animals, including humans, from radiation injury. In particular, the present invention provides methods and compositions comprising the isoflavone genistein (4',5,7-trihydroxyflavone) and other phytoestrogenic isoflavonoids.

BACKGROUND OF THE INVENTION

Radioprotective agents are compounds that reduce the biological effects of radiation (for review, see e.g., Hall, *Radiobiology for the Radiobiologist*, Lippincott Williams & Wilkins, Philadelphia, Pa. [1994]). They may be administrate before and/or after radiation exposure and can protect the organism from radiation-induced lethality. Radioprotectors have been shown to operate by a variety of different mechanisms (for review, see e.g., Bump and Malaker (eds.), *Radioprotectors: Chemical, Biological, and Clinical Perspectives*, CRC Press, Washington, D.C. [1997]). These include their antioxidant properties (Weiss and Landauer, Ann. NY Acad. Sci., 899:4460 [2000]), their estrogenic activity (Miernicki et al., Soc. Neurosci. Abstr., 16:1054 [1990]; and Patt et al., Amer. J. Physiol., 159:269-280 [1949]), and/or in some cases, their ability to inhibit protein kinase(s) involved in signal transduction (Liu et al., Oncogene, 19: 571-579 [2000]).

A variety of antioxidant compounds has been shown to confer radiation protection. These range from the highly toxic aminothiols to the antioxidant vitamins. However, the majority of these compounds have side effects of varying severity. For example, sulfhydryl radioprotectors such as amifostine (See e.g., U.S. Pat. No. 5,994,409) are highly toxic to mammals and must be administered in the hospital setting. Adverse side-effects associated with these compounds include nausea and vomiting, hypotension, hypocalcemia and drowsiness (Bienvenu et al., Adv. Exp. Med. Biol., 264:291-300 [1990]). Amifostine acts by scavenging free radicals (Murray, in Bump and Malaker, supra). Antioxidant vitamins (A, C, E and beta carotene) provide only minimal levels of radiation protection, have a very short window of protection, and if obtained from dietary sources, must be eaten in a variety of foods, since any single food source only has small levels of any vitamin (Weiss and Landauer, supra).

In addition, using presently used methods and compositions, it is necessary to administer single high doses of agents such as pharmaceuticals or other chemical additives by parenteral routes within a short time frame before or after the radiation or chemical insult (See e.g., Bump and Malaker, supra). Therefore, this precludes their use as a long-term prophylactic measure for use in protection against unanticipated radiation injury. Because of the short duration of action of most radioprotective agents, there has been a long and on-going search for agents that confer long lasting protection. Indeed, there remains a great need for a nontoxic, orally or parenterally available radioprotective agent that can be made available both before and after radiation injury.

SUMMARY OF THC INVENTION

Figure 1:
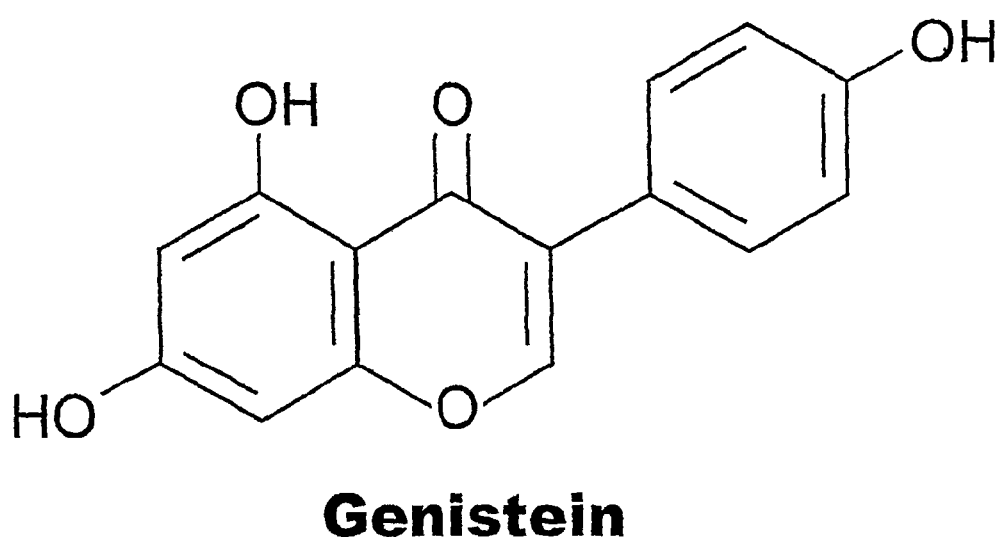
FIG. 1 shows the structure of the isoflavonoid genistein (4',5,7 trihydroxyflavone).

The present invention provides compositions and methods for the prophylactic and therapeutic treatment of animals, including humans, from radiation injury. In particular, the present invention provides methods and compositions comprising the isoflavone genistein (4',5,7-trihydroxyflavone) and other phytoestrogenic isoflavonoids.

The present invention provides methods for the radioprotection of a subject comprising providing a subject, a composition comprising at least one isoflavonoid, and a radiation source, administering the composition to the subject, and exposing the subject to radiation produced by a radiation source. In some preferred embodiments, the composition is administered to the subject before the subject is exposed to radiation, while in other preferred embodiments, the composition is administered to the subject after the subject has been exposed to radiation. In particularly preferred embodiments, the subject is protected from tissue damage from radiation. In some preferred embodiments, the subject is normal, while in other preferred embodiments, the subject is suffering from disease or another abnormality. In additional embodiments, the isoflavonoid(s) is selected from the group consisting of genistin, genistein, 6"-O-Mal genistein, 6"-O—Ac genistein, daidzein, 6"-O'Mal daidzein, 6"-O—Ac daidzein, glycitein, glycitin, 6"-O-Mal glycitin, biochannin A, formononetin, and mixtures thereof. In some embodiments, the isoflavonoid(s) is an antioxidant. In still further embodiments, the isoflavonoid(s) has estrogenic activity, while in alternative embodiments, the isoflavonoid(s) is a tyrosine kinase inhibitor. In additional embodiments, the isoflavonoid(s) comprises an angiogenesis inhibitor. In yet other embodiments, isoflavonoid(s) lowers the low-density lipoprotein concentration in the blood of the subject, and in other embodiments, the isoflavonoid(s) comprises a vasodilatory agent. In some preferred embodiments, the isoflavonoid is obtained from a source selected from the group consisting of soy, soy products and clover. In particularly preferred embodiments, the isoflavonoid is selected from the group consisting of genistin, genistein conjugates, genistein derivatives, genistein analogues, natural genistein, and synthetic genistein. In still other preferred embodiments, the isoflavonoid is dissolved in a vehicle. In some particularly preferred embodiments, the vehicle is polyethylene glycol. In additional embodiments, the composition further comprises one or more pharmaceutically acceptable carriers, excipients, auxiliaries, and diluents.

In some embodiments of the methods, the composition is systemically administered. Some preferred embodiments, the composition is administered in a pharmaceutically acceptable form, while in other preferred embodiments, the composition is administered in the diet of the subject or as a dietary supplement administered to the subject. In some embodiments, the composition is administered to the subject in a single dose, while in other embodiments, the composition is administered to, the subject in multiple doses. In preferred embodiments, the administering is selected from the group consisting of subcutaneous injection, oral administration, intravenous administration, rectal administration, vaginal administration, topical administration, intramuscular administration, intranasal administration, transdermal administration, subconjunctival administration, intraocular administration, periocular administration, retrobulbar administration, subretinal, suprachoroidal administration, and intrathecal administration. In alternative embodiments, the administering is administration from a source selected from the group consisting of mechanical reservoirs, devices, implants, and patches. In still further embodiments, the composition is in a form selected from the group consisting of pills, capsules, liquids, gels, powders, suppositories, suspensions, creams, jellies, aerosol sprays, and dietary supplements. In some preferred embodiments, the dietary supplement comprises an unprocessed soy food, while in other preferred embodiments, the dietary supplement comprises isolated soy protein. In additional embodiments, the isoflavonoid is a natural ingredient of a dietary component.

In some embodiments, the composition comprises from about 0.1 mg to about 2000 mg isoflavonoid. In some preferred embodiments, the dosage of the composition administered to the subject is from about 5 mg/day to about 2000 mg/day isoflavonoid, while in other preferred embodiments, the dosage of the composition administered to the subject comprises from about 25 mg/day to about 1200 mg/day isoflavonoid, or from about 40 mg/day to about 1200 mg/day isoflavonoid, or in yet further embodiments, the dosage of the composition administered to the subject comprises from about 30 mg/day to about 200 mg/day isoflavonoid. In other embodiments, the composition is administered to the subject is in a dosage of an effective amount less than about 400 mg/kg/day of the body weight of the subject. In some preferred embodiments, the composition is administered to the subject is in a dosage of an effective amount from about 1 mg/kg/day to 20 mg/kg/day of the body weight of the subject.

In some embodiments, the composition is administered from about 10 minutes to 96 hours before radiation exposure. In some additional embodiments, the composition is administered as a single dose, while in other embodiments the composition is administered in multiple doses of the same or varying concentration of isoflavonoid(s). In other embodiments, the composition is administered from about 1 minute to 48 hours after radiation exposure. In some embodiments, the radiation is selected from the group consisting of ionizing radiation, alpha radiation, beta radiation, gamma radiation, neutrons, microwaves, and electromagnetic radiation.

The present invention also provides nontoxic radiation protective compositions comprising a therapeutically effective amount of at least one nontoxic, phytoestrogenic isoflavonoid selected from the group consisting of genistin, genistein, 6"-O-Mal genistein, 6"-O—Ac genistein, daidzein, 6"-O-Mal daidzein, 6"-O—Ac daidzein, glycitein, glycitin, 6"-O-Mal glycitin, biochanin A, formononetin, and mixtures thereof. In some preferred embodiments, the therapeutically effective amount is a prophylactically effective amount.

The present invention further provides methods for preparing nontoxic, radiation-protective compositions comprising at least one isoflavonoid, comprising the steps of dissolving an isoflavonoid selected from the group consisting of genistin, genistein, 6"-O-Mal genistein, 6"-O—Ac genistein, daidzein, 6"-O-Mal daidzein, 6"-O—Ac daidzein, glycitein, glycitin, 6"-O-Mal glycitin, biochanin A, formononetin, and a mixture thereof in a vehicle selected from the group consisting of polyethylene glycol (PEG) and sesame oil vehicle to produce a suspension; and separating the isoflavonoid of the suspension to produce an isoflavonoid solution. In some embodiments, the composition further comprises at least one additional ingredient selected from the group consisting of pharmaceutically acceptable carriers, excipients, auxiliaries, and diluents.

DESCRIPTION OF THE INVENTION

The present invention provides compositions and methods for the prophylactic and therapeutic treatment of animals, including humans, from radiation injury. In particular, the present invention provides methods and compositions comprising the isoflavone genistein (4',5,7-trihydroxyflavone) and other phytoestrogenic isoflavonoids.

Indeed, the present invention provides means to reduce the mortality associated with radiation exposure by animals, including humans. Accordingly, the present invention provides a method for prophylactic and therapeutic treatment of radiation damage to animals, including humans.

In particularly preferred embodiments, the present invention provides nontoxic, naturally occurring dietary supplements for the use as radiation protective agents. However, it is not intended that the present invention be limited to dietary supplements, as the present invention finds use through various other means of administration, including but not limited to subcutaneous, intramuscular, intravenous, etc.

Figure 2:
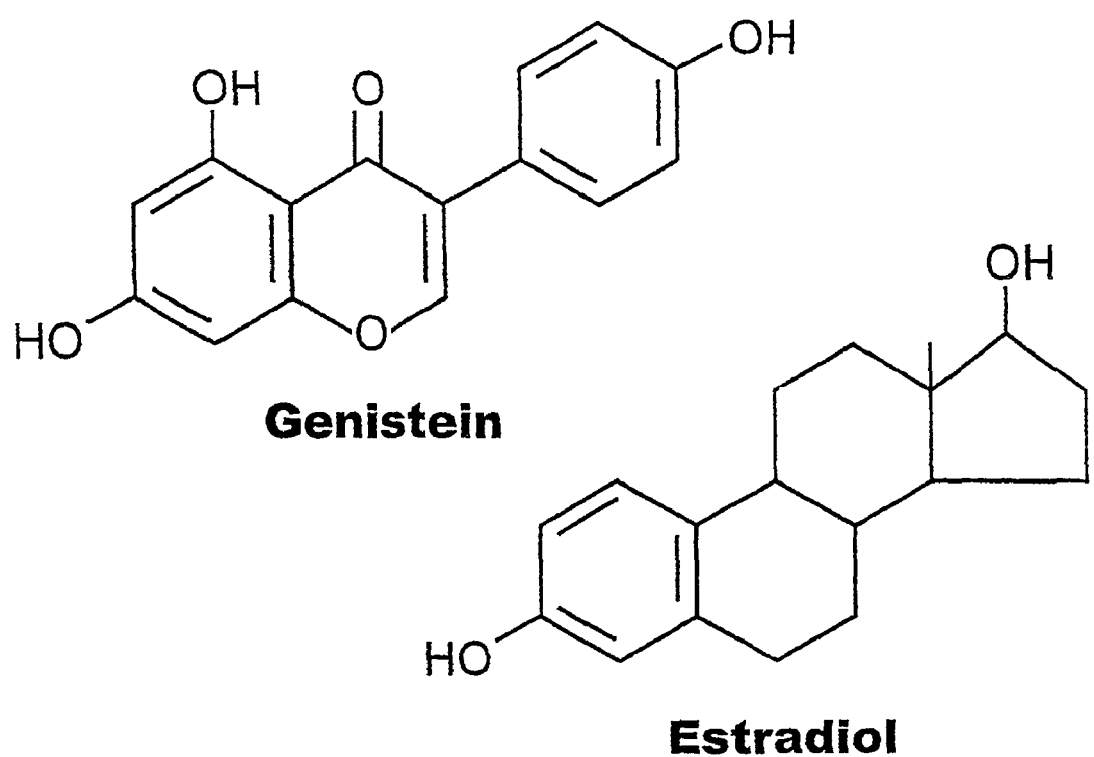
FIG. 2 shows the structure of the phytoestrogen genistein showing similarities with the structure of the hormone estradiol.

Other compounds have been investigated for their radioprotective properties. For example, estrogen has been found to reduce radiation-induced lethality (Miernicki et al., supra; Patt et al., supra). However, Miernicki et al. reported that radioprotective doses of the estrogen 17-beta-estradiol were behaviorally toxic. As a phytoestrogen (Messina, Am. J. Clin. Nutr., 70 (3 Suppl): 439S-450S [1999]), it was believed that genistein may have enough estrogenic activity to be protective, but not as to be toxic. A comparison of the similarities in structure of genistein and estradiol are illustrated in FIG. 2.

I. Genistein

As indicated herein, genistein (4',5,7-trihydroxyflavone) (See, FIG. 1) is considered a potent antioxidant (Wei et al., Proc. Soc. Exp. Biol. Med., 208:124-30 [1995]). Genistein also inhibits DNA topoisomerase II, cell cycle progression, and angiogenesis. In addition, it has been shown to be a vasodilatory agent and to reduce LDL (low-density lipoprotein) cholesterol levels. Indeed, these properties were the bases of studies investigating alternative mechanisms of genistein's protective action (Kim, Am. J. Clin. Nutr., 68:1418 S-1425S [1998]). Furthermore, ionizing radiation-induced apoptosis (programmed cell death) is triggered by tyrosine kinase activation. Genistein, as an inhibitor of protein tyrosine kinases, has been shown to prevent radiation-induced cell death (Uckun et al., Clin. Canc. Res., 4:1125-34 [1998]). Therefore, protein kinase inhibitors such as genistein were investigated as candidate radioprotective agents during the development of the present invention.

However, in contrast to the present invention, in which genistein is utilized to prolong the survival of an animal following exposure to radiation, genistein has been investigated as an adjunct therapy for cancer treatment to enhance the killing and/or suppression of tumor cells. For example, genistein, in conjunction with X-rays, was found to cause an enhancement of radiation-induced cell death (van Rijn and van den Berg, Clin. Canc. Res., 3:1775-9 [1997]). The soybean-derived Bowman-Birk Inhibitor (BBI), a protease inhibitor not related to the isoflavone genistein, suppresses x-ray induced transformation of cells but does not protect human lung cancer cells from radiation-induced cytotoxicity. In fact, treatment with the BBI inhibitor actually enhanced cell killing by cisplatin in combination with radiation treatment in the lung carcinoma cells (Kennedy et al., Nutr. Canc., 26:209-17 [1996]).

U.S. Pat. No. 5,824,702, discusses the use of genistein to protect the skin from ultraviolet radiation. However, this Patent is limited to the topical application of genistein for protection against ultraviolet radiation. Ultraviolet radiation, because it is less capable of penetrating through matter than is visible light, is considered for all practical purposes to be non-ionizing (See e.g., Attix, *Introduction to Radiological Physics and Radiation Dosimetry*. John Wiley & Sons, New York [1986]). Moreover, the window of efficacy for this use of genistein is indicated as being limited to two hours. Thus, the use of a protectant that must be applied to the skin and has a short window of efficacy against essentially non-ionizing radiation is quite different from the protectant of the present invention which protects against highly penetrating ionizing radiation (e.g., gamma rays).

U.S. Pat. No. 6,071,956, discusses the use of flavonoids as inhibitors of heat shock protein, the formation of which is an injurious biological consequence of tissue stress. Radiation is cited among the applicable stressors, however, this Patent is limited to inhibiting radiation-induced heat shock proteins as they relate to smooth muscle tissue injury.

II. Radioprotection

During the development of the present invention, genistein was found to have the characteristics of an ideal radioprotectant. However, it is contemplated that additional compounds will find use in the present invention (e.g., daidzein and glycitein and their metabolites). Advantages to the use of genistein include its nontoxic, antioxidant, phytoestrogenic, protein tyrosine kinase inhibitor properties. In addition, it is a natural product available in the diet from a single food source, and can be given daily to provide a long window of protective efficacy. Furthermore, it can be easily administered and has an established long shelf life.

Nonetheless, prior to the development of the present invention, the use of genistein to provide effective radiation protection against and/or ameliorating the potentially lethal effects of ionizing radiation was apparently unknown, as no reference discusses the use of genistein to protect animals from ionizing radiation injury or death. Although an understanding of the mechanism(s) is not necessary in order to use the present invention, it is believed that the combination of the antioxidative, estrogenic, and protein tyrosine-kinase inhibitory properties of genistein provides protection from ionizing radiation injury or death.

Shimoi and colleagues (Shimoi et al., Carcinogenesis, 15:2669-72 [1994]), reported that a single gastric intubation of a variety of flavonoids, including genistein, given six hours before irradiation, reduced the frequency of micronucleated reticulocytes in peripheral blood of mice. However, whole organism radioprotection was never demonstrated or mentioned. Indeed, Shimoi's work was limited to investigations of cells, rather than an entire animal.

Uma and colleagues (Uma et al., Radiat. Res., 151:74-8 [1999]) reported that two flavonoids, orientin and vicenin, isolated from the leaves of a medicinal plant, offered some protection (60-67% survival) when intraperitoneally (IP) administered to mice 30 minutes before a radiation dose 1.3 Gy above the $LD_{50}$. The compounds were less effective (30-35% protection) when given orally, intravenously, or intramuscularly. Agents administered to mice by IP injection often confer the best protection presumably because drugs can be absorbed directly from the peritoneal fluid. In humans, however, IP is not a normal route for drug administration. In addition, the compounds had a limited time window of efficacy before irradiation (30-60 minutes, as compared with 1-4 day efficacy provided by the present invention) and were not effective at all if given after radiation. Furthermore, they were not evaluated under a multiple dose regimen or via the subcutaneous route, which are common methods of delivery in humans. However, in the present invention, survival of multiple doses of oral genistein administration resulted in survival of 69% at a radiation dose comparable to that of Uma et al., where only 30-35% survival was obtained. Moreover, in the present invention, using the subcutaneous route of administration 100 and 400 mg/kg doses of genistein provided survival rates of 81% and 88%, respectively. This is a substantial increase in radioprotection over that reported for the non-isoflavone flavonoids evaluated by Uma et al. In addition, the compounds Uma et al. evaluated have no documented estrogenic or protein tyrosine kinase inhibitory activity. In contrast, although an understanding of the mechanism(s) is not necessary in order to use the present invention, and it is not intended that the present invention be so limited, it is contemplated that the superior efficacy of genistein is due to a synergistic effect of combined antioxidant, estrogenic, and protein tyrosine kinase inhibitory properties.

As indicated in the Examples, experiments conducted during the development of the present invention clearly show that the isoflavone genistein is a very effective radiation protective agent. As discussed, it was shown to protect against radiation-induced lethality and enhance survival when administered one day before radiation exposure, by both the oral and subcutaneous routes of administration. In addition, if given in multiple oral doses, genistein enhances 30-day survival when given both 4 days before, as well as 4 days before and 4 days after a lethal dose of gamma radiation, thus providing a long window of protective efficacy. Importantly, behavioral tests demonstrated that at all doses (50-400 mg/kg) evaluated, genistein did not result in any behavioral toxicity. Thus, experiments conducted during the development of the present invention led to the development of novel combinations of nontoxic, natural food sources, with effective radioprotection, and a long window of protection.

The present invention finds wide use in various settings. Indeed, it finds use anywhere where radiation is likely to be a problem. For example, the present invention finds use in protection against a solar radiation event, such as those potentially experienced by astronauts (Parsons and Townsend, Radial. Res., 153:729-33 [2000]), as well as by pilots and other flight personnel that make frequent high altitude trips where radiation exposure is a potential hazard (Bottollier-Depois et al., Radial. Res., 153:526-32 [2000]). In addition, the present invention finds use in conjunction with radiation therapy in the clinic, nuclear power plant facilities, food radiation plants, and in cleanup of radiation dump sites and accidents (e.g., such as those experienced in Chernobyl, Ukraine, Tokaimura, Japan, and Three-Mile Island, U.S.). It is also contemplated that the present invention will find use by the military in the event of a nuclear radiation event, as well as by civilian civil defense personnel in response to a terrorist radiation event. It is further contemplated that the present invention will find use in reducing the toxic effects of inhaled radionuclides and in reducing toxicity from radiation produced by electronic devices such as cellular phones.

It is further contemplated that because reactive oxygen species and related free radicals may be generated with equal effect as a result of both radiation and chemotherapy, antioxidant isoflavonoids such as genistein will find use as effective agents in mitigating the toxic effects of chemotherapy. "Chemoprotection" refers to protection from chemicals such as chemotherapeutic agents exemplified by cisplatin and the like.

The present invention provides ideal protective agents, as they are nontoxic, produce no behavioral alterations or other side effects, are naturally occurring, have minimal cost, and a long shelf life. In addition, the compositions of the present invention are suitable for daily use. Therefore, diet-derived products that offer the radiation and chemoprevention of the present invention are contemplated to find widespread long-term use (Kelloff et al., J. Nut., 130(2S Suppl):467S-471S [2000]).

III. Preferred Embodiments

In some preferred embodiments, the present invention provides methods that comprise the administration of an isoflavone in an amount sufficient to treat radiation injury prophylactically or therapeutically. Although it is contemplated that any isoflavone will find use in the present invention, in preferred embodiments, genistein, a related isoflavonoid or metabolite with the same properties (e.g., excellent antioxidant properties and estrogenic properties) are used. In an alternative embodiments, the related isoflavonoid or metabolite has protein kinase activity.

The isoflavone protector, preferably genistein, can be administered by any suitable route. Genistein may be administered by mouth (per os), by injection, in the diet, or by any number of other systemic routes. The isoflavone protector can be administered either singly or in multiple dosing regimens either before or before and after exposure to ionizing radiation. For the prophylactic treatment of radiation injury, the isoflavone is administered preferably orally or by subcutaneous injection. If given orally, in particularly preferred embodiments, it is administered from about 24 or more hours before the radiation exposure and repeated dosing of this compound, by appropriate dietary means or other means is preferred. However, it is not intended that the present invention be limited to this particular time frame, as in sonic cases, oral administration less than 24 hours prior to radiation exposure is preferred. When administered subcutaneously, single administration 1-24 hrs before exposure is suitable. However, it is not intended that the present invention be limited to this particular time frame, as in some cases, subcutaneous administration less or more than 24 hours prior to radiation exposure is preferred. Regardless of the route of administration, in some embodiments, increased beneficial effects are observed if continued after the radiation event.

In addition to the active ingredients, the compositions may of the present invention contain suitable carriers comprising excipients and auxiliaries which facilitate processing of the active compounds into preparations which can be used either in dietary supplements, foods, feeds, and/or as pharmaceutical preparations. Further details on techniques for formulation and administration for pharmaceutical preparations may be found in the latest edition of *Remington's Pharmaceutical Sciences* (Maack Publishing Co., Easton, Pa.).

In addition to dietary administration (i.e., in food, feed, dietary supplements, etc.), pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients include carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage).

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers. Thus, any suitable vehicle finds use in the present invention.

Dietary and pharmaceutical formulations suitable for parenteral administration may be formulated in aqueous solutions preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Dietary and pharmaceutical compositions of the present invention may be manufactured in a manner that is known in the art (e.g., by means of conventional mixing, dissolving, granulating, dragee-making, levigating, emulsifying, encapsulating, entrapping, or lyophilizing processes).

After the dietary and pharmaceutical compositions have been prepared, they are placed in an appropriate container and labeled for treatment of an indicated condition. For administration of genistein, such labeling would include amount, frequency, and method of administration.

Dietary and pharmaceutical compositions suitable for use in the present invention include compositions wherein the active ingredients are contained in an effective amount to achieve the intended purpose. The determination of an effective dose is well within the capability of those skilled in the art.

For any compound, the prophylactically and/or therapeutically effective dose can be estimated initially either in cell culture assays (e.g., of neoplastic cells), or in animal models, usually mice Animal models may also be used to determine the appropriate concentration range and route of administration. Such information is then used to determine useful doses and routes for administration in humans.

As indicated herein, prophylactically and therapeutically effective doses refer to that amount of active ingredient (e.g., genistein) which ameliorates the symptoms and/or effects of radiation. Efficacy and toxicity may be determined by standard pharmaceutical procedures in cell cultures or experimental animals (e.g., $ED_{50}$, namely, the dose that is therapeutically effective in 50% of the population), and $LD_{50}$ (i.e., the dose that is lethal to 50% of the population). The dose ratio between therapeutic and toxic effects is the "therapeutic index," and it can be expressed as the ratio, $LD_{50}/ED_{50}$.

Pharmaceutical compositions which exhibit large therapeutic indices are preferred. The dosage contained in such compositions is preferably within a range of circulating concentrations that include the $ED_{50}$ with little or no toxicity. The dosage varies within this range depending upon the dosage form employed, sensitivity of the patient, and the route of administration. One advantage of the present invention is low toxicity. Thus, the therapeutic index for compounds such as genistein is quite high.

The exact dosage used with each subject is typically determined either by the subject, medical profession (e.g., physician, nurse, etc.), and/or nutritionist/dietary counselor, taking into consideration factors related to the subject that requires treatment. Dosage and administration are adjusted to provide sufficient levels of the active moiety or to maintain the desired effect. Factors which may be taken into account include the severity of the disease state, amount of radiation exposure experienced or to be experienced, general health of the subject, age, weight, and gender of the subject, diet, time and frequency of administration, drug combination(s), reaction sensitivities, and tolerance/response to therapy.

Typically, dosage amounts vary from about 5 to 2000 mg/day, or at levels up to approximately 16 mg/kg/day. In some embodiments, lower concentrations are preferred (e.g., 600-1200 mg/day). While in still further embodiments, even lower concentrations are preferred (e.g., about 200 mg/day). Indeed, the dosage amounts vary, depending upon the patient, as indicated above. Guidance as to particular dosages and methods of delivery is provided in the literature and generally available to practitioners in the art.

It is contemplated that the present invention will benefit the world community. Indeed, the present invention provides the additional protection against the potential threats of insults from the innocent or intentional exposure of the population to the harmful effects of radiation. The source of this exposure can range from the rapid growth in the use of radiation emitting household appliances, medical devices and high powered electrical transmission systems, including wireless communication systems or devices (i.e., cell phones) to the threat of nuclear disasters.

DEFINITIONS

As used herein, the term "animal" refers to any animal, including humans. The term "non-human animal" includes vertebrates and invertebrate animals, including but not limited to rodents, arthropods, insects, fish, non-human primates, ovines, bovines, ruminants, lagomorphs, porcines, caprines, equines, canines, felines, ayes, etc. In preferred embodiments, the term refers to mammals, while in particularly preferred embodiments, the term refers to humans.

As used herein, the term "subject" refers to any animal, including, but not limited to humans. However, in preferred embodiments, the animal is a mammal (e.g., humans, rodents, non-human primates, ovines, bovines, ruminants, lagomorphs, porcines, caprines, equines, canines, felines, etc.). In some embodiments, the subject is "normal," while in other embodiments, the subject is suffering from pathology (e.g., infectious disease, cancer, genetic or inherited diseases, etc.). In particularly preferred embodiments, the subject is treated using the method(s) and composition(s) of the present invention.

As used herein, the term "treatment" refers to the administration of the radioprotective composition in an amount that is effective in preventing injury to an animal who has been or will be exposed to radiation. Thus, in some embodiments, the term encompasses the administration of the radioprotective composition prior to the exposure of the animal to radiation (i.e., "prophylactic" administration), while in other embodiments the term encompasses treating an animal after the animal has been exposed to the radiation (i.e., "therapeutic" administration). In still further embodiments, the term encompasses the continuation of the amelioration of the injury long after the radiation exposure.

As used herein, the term "antioxidant" refers to compounds that have the ability to slow the oxidation rate of oxidizable substances, in particular those that are autoxidizable. Antioxidants act through several chemical and physiological means, including chelation with metal ions, scavenging of free radicals, and termination of chain reactions that occur during lipid peroxidation.

As used herein, the term "phytoestrogen" refers to weak estrogenic compounds produced by plants.

As used herein, the term "flavonoid" refers to a group of phenolic compounds found in fruits and vegetables. The basic structure of flavonoids consists of two benzene rings linked through a heterocyclic pyran ring (See e.g., Kuo, Organogenesis 8:47-69 [1997]).

As used herein, the term "isoflavonoid" refers to a subclass of flavonoids characterized by the presence of a second benzene attached to the C3 position of C2. These compounds include genistein, daidzein, glycitein, as well as their glucosides and metabolites. In addition, the subclass includes 4-methyl ether derivatives of genistein and daidzein, biochanin A, and formonectin, as well as genistin, 6"-O-Mal genistein, 6"-O—Ac genistein, 6"-O-Mal daidzein, 6"-O—Ac daidzein, glycitin, and 6"-O-Mal glycitin.

As used herein, the term "radiation" refers to any form of electromagnetic radiation. Absorbed doses are typically measured in "grays" (Gy).

As used herein, the term "ionizing radiation" refers to radiation that has sufficient energy to eject one or more orbital electrons from an atom or molecule (e.g., $\alpha$ particles, $\beta$ particles, $\gamma$ rays, x-rays, neutrons, protons, and other particles having sufficient energy to produce ion pairs in matter.

As used herein, the term "vehicle" refers to any composition that is suitable for use as a diluent, solvent, or other composition suitable for producing a suspension of a compound of interest. In preferred embodiments, the vehicle is a liquid, colloidal, or semi-solid composition, such as water, polyethylene glycol, oil (e.g., sesame oil), or other liquid suitable for producing a suspension comprising at least one flavonoid or isoflavonoid. In some embodiments, the vehicle of the present invention is a solid that contains at least one isoflavonoid or flavonoid. Thus, the term also encompasses dietary sources (including dietary supplements) of genistein and/or other flavonoids.

The term "mixture" refers to a mingling together of two or more substances without the occurrence of a reaction by which they would lose their individual properties. The term "solution" refers to a liquid mixture. The term "aqueous solution" refers to a solution that contains some water. In many instances, water serves as the diluent for solid substances to create a solution containing those substances. In other instances, solid substances are merely carried in the aqueous solution (i.e., they are not dissolved therein). The term aqueous solution also refers to the combination of one or more other liquid substances with water to form a multi-component solution.

The term "parenterally" refers to administration to a subject through some means other than through the gastrointestinal tract. The most common mode of parenteral administration is intravenous. However, other modes of parenteral administration include, but are not limited to, intramuscular, intradermal, intrathecal, intranasal and subcutaneous administration.

As used herein, the term "pharmaceutical composition" refers to compositions composed of one or more pharmaceutically acceptable diluents, excipients or carriers. As used herein, the phrase "pharmaceutical preparation suitable for parenteral administration" refers to a solution containing at least one flavonoid and/or isoflavonoid compound in a pharmaceutically acceptable form for parenteral administration. The characteristics of the form will depend on a number of factors, including the mode of administration: For example, a preparation for intravenous administration will often comprise the compound dissolved in normal saline or sterile water for injection. Of course, the pharmaceutical preparations of the present invention are not limited to those diluents; indeed, other components or diluents known in the field of pharmaceuticals and pharmacy are within the scope of the present invention. The pharmaceutical preparation may contain diluents, adjuvants and excipients, among other components, provided that those additional components neither adversely effect the preparation (e.g., they do not cause degradation of the compound) nor the recipient (e.g., they do not cause a hypersensitivity reaction).

As used herein, the term "topically active agent" indicates a substance or composition which elicits a pharmacologic response at the site of application. In preferred embodiments, the agent is a radioprotective composition, while in particularly preferred embodiments, the agent is genistein.

As used herein, the term "systemically active agent" is used broadly to indicate a substance or composition which will produce a pharmacologic response at a site remote from the point of application. In preferred embodiments, the agent is a radioprotective composition, while in particularly preferred embodiments, the agent is genistein.

As used herein, the term "medical devices" includes any material or device that is used on, in, or through a patient's body in the course of medical treatment for radiation therapy. Medical devices include, but are not limited to, such items as medical implants, drug delivery devices, and body cavity and personal protection devices. The medical implants include, but are not limited to, urinary catheters, intravascular catheters, dialysis shunts, skin sutures, vascular grafts, implantable meshes, intraocular devices, heart valves, and the like.

As used herein, the term "dietary supplement" refers to as product that contains one or more of the following dietary ingredients: a vitamin, a mineral, an herb or other botanical, an amino acid, a dietary substance for use by humans and other animals to supplement the diet by increasing the total dietary intake, and/or a concentrate, metabolite, constituent, extract of any of these ingredients. Thus, it is intended that the term encompass any dietary supplement that comprises a flavonoid, in particular isoflavonids such as genistein. It is not intended that the present invention be limited to any particular dietary supplement(s), as the flavonoid of the present invention finds use as a dietary supplement administered alone or in combination with other dietary supplements.

As used herein, the terms "food" and "feed" refer to food suitable for human and/or non-human animal use. The terms encompass liquid, solid, semi-solid, and other nutritional substances.

As used herein, the term "diet" refers to the nutritional intake of a subject (e.g., an animal). It is intended that the term encompass food, feed, dietary supplements, and other items ingested by a subject to meet nutritional, energy, and other bodily requirements.

The term "substantially purified," as used herein, refers to a compound that is removed from its natural environment, isolated or separated, and are at least 60% free, preferably 75% free, and most preferably 90% free from other components with which it is naturally associated. In some embodiments, the term refers to compounds synthesized in the laboratory in which the compound is at least 60% free, preferably 75% free, and most preferably 90% free from other components with which it is associated during the synthetic process.

As used herein, the term "purified" refers to the removal of contaminants from a sample. Methods such as carbon, hydrogen and nitrogen analyses (CHN analysis, or "elemental analysis") may be used to determine the purity of compounds. In preferred embodiments, the CHN values of compounds of the present invention are very close to the predicted values. Correspondence of experimental with the predicted values to within 0.3% indicates high levels of purity.

EXPERIMENTAL

The following Examples are provided in order to demonstrate and further illustrate certain preferred embodiments and aspects of the present invention and are not to be construed as limiting the scope thereof.

In the experimental disclosure which follows, the following abbreviations apply; eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); l or L (liters); ml (milliliters); µl (microliters); cm (centimeters); mm (millimeters); µm (micrometers); nm (nanometers); Gy (gray or grays; 1 Gy=100 rad); po (per os; by mouth); sc (subcutaneous); iv (intravenous); ip (intraperitoneal); im (intramuscular); ° C. (degrees Centigrade); Sigma (Sigma Chemical Co., St. Louis, Mo.); Charles River (Charles River, Raleigh, N.C.); Jackson (Jackson Laboratory, Bar Harbor, Me.); Boehringer Mannheim (Boehringer Mannheim, Indianapolis, Ind.); Fisher (Fisher Scientific, Pittsburgh, Pa.); Life Technologies (Life Technologies, Rockville, Md.); Abbott (Abbott Laboratories, North Chicago, Ill.); Ultrasonics (Ultrasonics, Plainview, N.Y.); Omnitech (Omnitech Electronics, Columbus, Ohio); Chatillon (Chatillon, Greensboro, N.C.).

The examples presented herein are intended to be illustrative in nature and in no way intended to limit the scope of this invention.

In the experiments described herein, male CD2F1 mice (Charles River) weighing 24-30 grams were used. All mice were quarantined on arrival and representative animals were screened for evidence of disease. Mice were housed in a facility accredited by the Association for Assessment and Accreditation of Laboratory Animal Care International. Animal rooms were maintained at 21+/−2° C., with 50%+/−10% humidity on a 12/12 hr light/dark cycle. Commercial rodent ration (Harlan Teklad Rodent Diet 8604) was freely available as was acidified (pH, 2.5-2.8) water to control opportunistic infections (See, McPherson, Lab. Animal Care, 13:737-44 [1963]). Mice were housed in polycarbonate cages in groups of eight.

In the experiments described herein, compounds: Control groups received either saline (Abbott) or the drug vehicle, polyethylene glycol with a molecular weight of 400 (PEG). PEG vehicle and genistein were obtained from Sigma. PEG is a viscous, slightly hygroscopic liquid, which finds wide use in food and food packaging as well as in the pharmaceutical industry. During the development of the present invention, several studies were conducting involving drugs dissolved in PEG-400 because of its high solubility and low radioprotective characteristics. However, there appeared to be no reports in which genistein has been solubilized in PEG-400. After many attempts to solubilize genistein, it was determined that after brief sonication (10 seconds, medium pulse) using a sonicator cell disrupter (Model W255R, Heat Systems Ultrasonics), high concentrations of genistein could be easily solubilized in PEG-400. Thus, 100 mg genistein was solubilized in 1 ml of PEG-400 for these experiments. The solution obtained was injected sc at 0.1 ml/mouse or diluted to 0.25 ml/mouse for oral administration. This concentration corresponds to 400 mg/kg body weight for a 25 gram animal.

In Examples 1-3 below, mice were irradiated in the bilateral gamma-radiation field of the Armed Forces Radiobiology Research Institute cobalt-60 facility (Carter and Verrelli, AFRRI cobalt whole-body irradiation (Technical Report 73-3); Bethesda, Md.: Armed Forces Radiobiology Research Institute [1973]). The midline tissue (MLT) dose to the animals was 8.5-9.5 Gy. The dose rate was 0.6 Gy/min. The dose rate was established in an acrylic mouse phantom by use of a 0.5-cc, tissue-equivalent ionization chamber (calibration factor traceable to the National Institute of Standards and Technology). The dose conversion factor (DCF) 0.96 and the field were uniform to within +/−3%. Dose measurements followed the American Association of Physicists in Medicine protocol (American Association of Physicists in Medicine, Med. Phys., 10:741-771 [1983]). MLT doses were determined by applying the DCF to dose measurements made free in air (FIA). The DCF was determined by taking the ratio of two measurements. The first measurement was the MLT dose-rate taken at a well-defined point in the abdominal region of the phantom. The second measurement was the FIA tissue dose-rate, taken after removing the phantom, at a convenient point in the region that the phantom had occupied. Once determined for a particular experimental setup, the DCF value can be applied to all future FIA measurements to obtain the MLT dose-rate using the same setup.

Example 1

Protective Effects of a Single Oral Dose

This Example describes experiments to determine the protective effects of a single oral dose of genistein administered 1 or 24 hours before radiation mitigates radiation-induced mortality. The effects of genistein on radioprotection was evaluated after a single oral (po) dose of saline, PEG vehicle, or 400 mg/kg genistein (genistein-400) administered 1 hour or 24 hours before 8.5 Gy or 9.5 Gy cobalt-60 gamma radiation delivered at a dose rate of 0.6 Gy/min (N=16). Following irradiation, mice were returned to their home cages where survival was monitored for 30 days. The radiation. LD50/30 for male CD2F1 mice administered saline was determined to be approximately 8.3 Gy. The 30-day survival rate was analyzed using a Chi square test.

Figure 3:
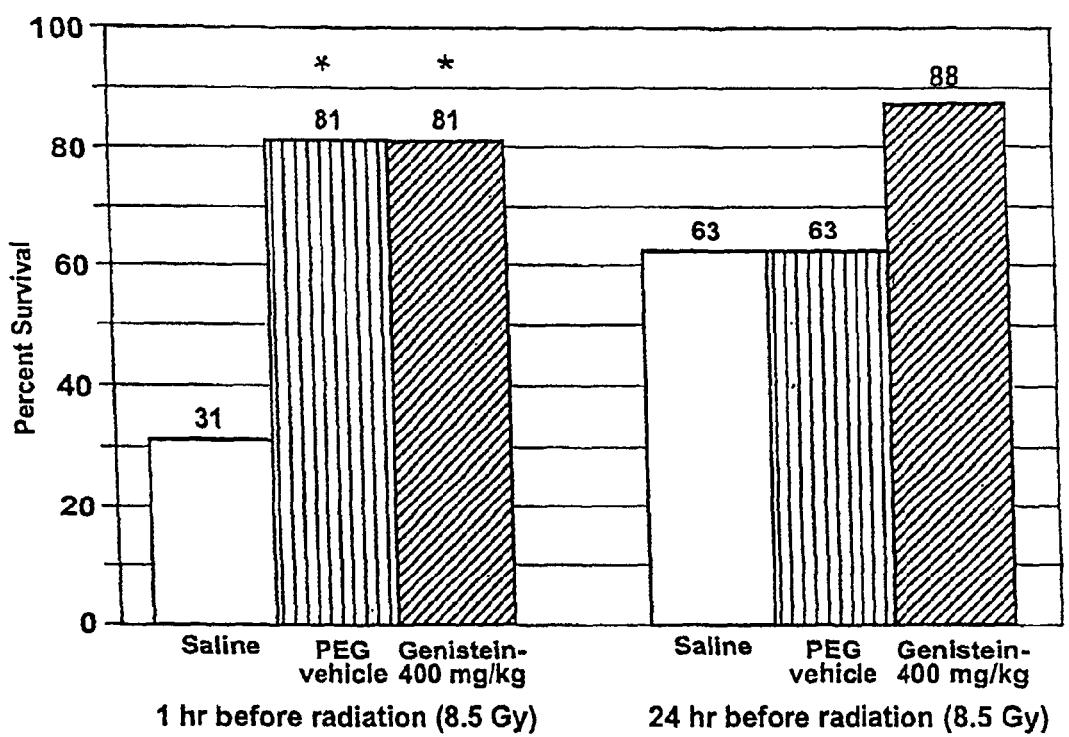
FIG. 3 shows the histogram for the effect of a single oral (po) administration of genistein on 30-day survival. Mice were given genistein either 1 hour or 24 hours before an 8.5 Gy dose of gamma radiation from a cobalt-60 source. The dose rate was 0.6-Gy/minute. Experimental groups consisted of saline, polyethylene glycol (PEG) vehicle, or genistein (400 mg/kg). While genistein did not offer protection 1 hour before radiation, 88% of mice that received genistein 24 hours survived, compared to 63% survival for the saline and PEG control groups (N=16/group). The asterisk indicates a significant difference from control.
Figure 4:
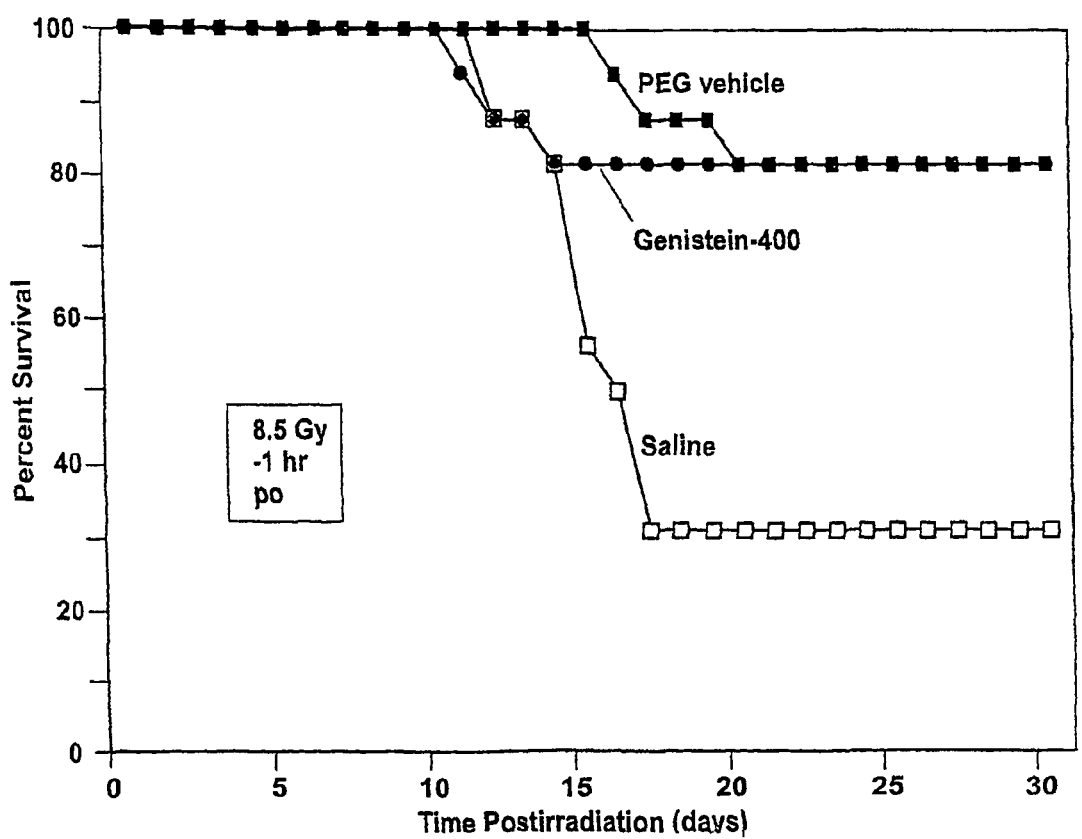
FIG. 4 shows the survival curve of mice administered a single oral (po) administration of saline, polyethylene glycol (PEG) vehicle, or 400 mg/kg genistein 1 hour before 8.5 Gy gamma radiation (N=16/group). Survival was monitored for 30 days postirradiation. This figure depicts the survival curve for the data illustrated in FIG. 3.
Figure 5:
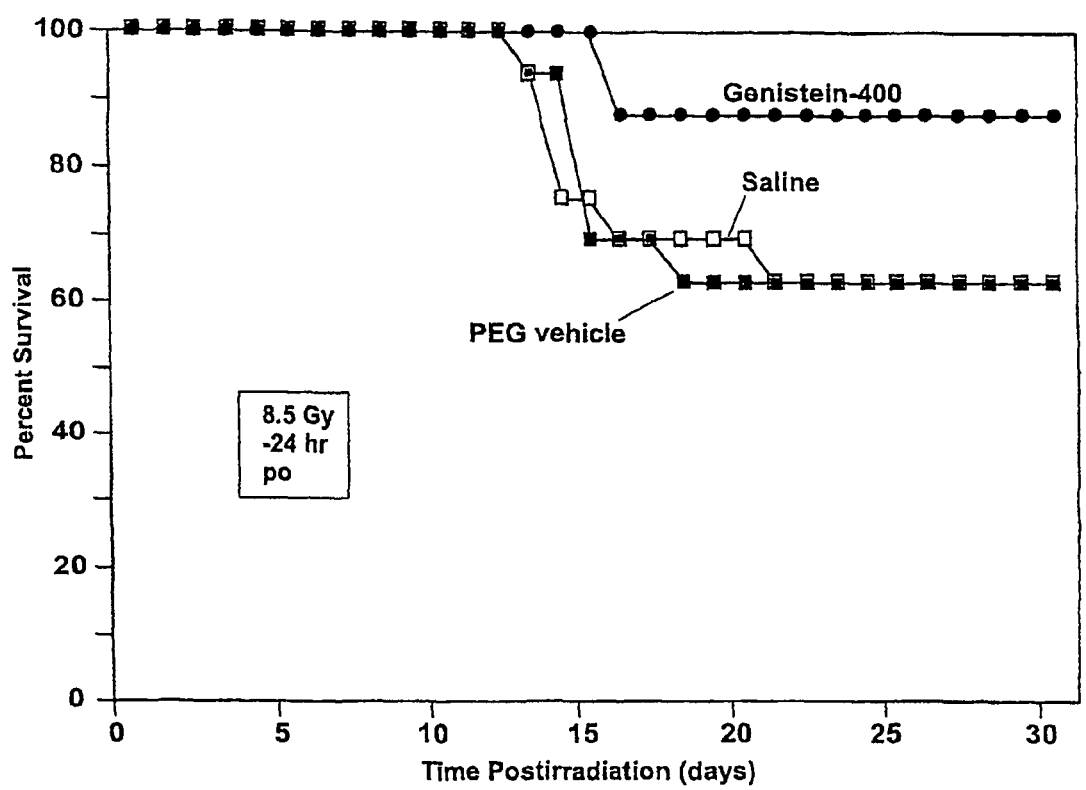
FIG. 5 shows the 30 day survival curve for mice administered a single oral (po) dose saline, polyethylene glycol (PEG) vehicle, or 400 mg/kg genistein 24 hours before 8.5 Gy gamma radiation (N=16, group). Survival was monitored for 30 days postirradiation. This figure depicts the survival curve for the data illustrated in FIG. 3.
Figure 6:
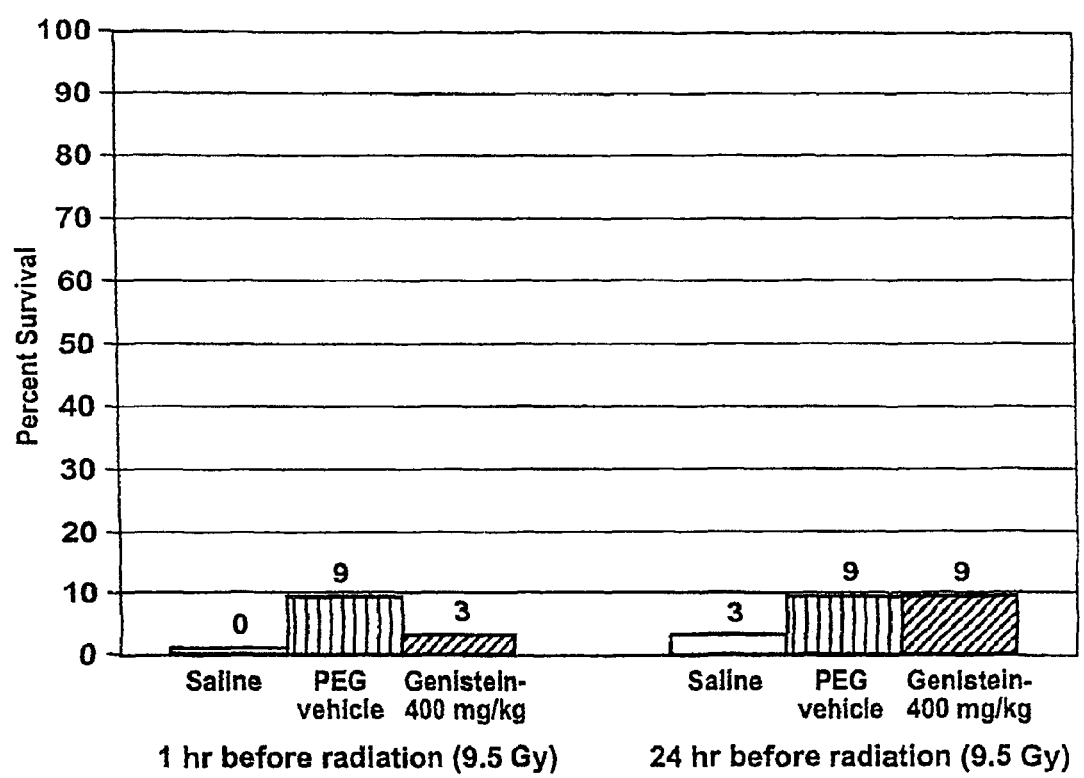
FIG. 6 shows the histogram for the effect of a single oral (po) administration of genistein on 30-day survival of mice given genistein either 1 hour or 24 hours before a 9.5 Gy dose of gamma radiation from a cobalt-60 source. The dose rate was 0.6 Gy/minute. Experimental groups consisted of saline, polyethylene glycol (PEG) vehicle, or genistein (400 mg/kg) (N=24-32/group).
Figure 7:
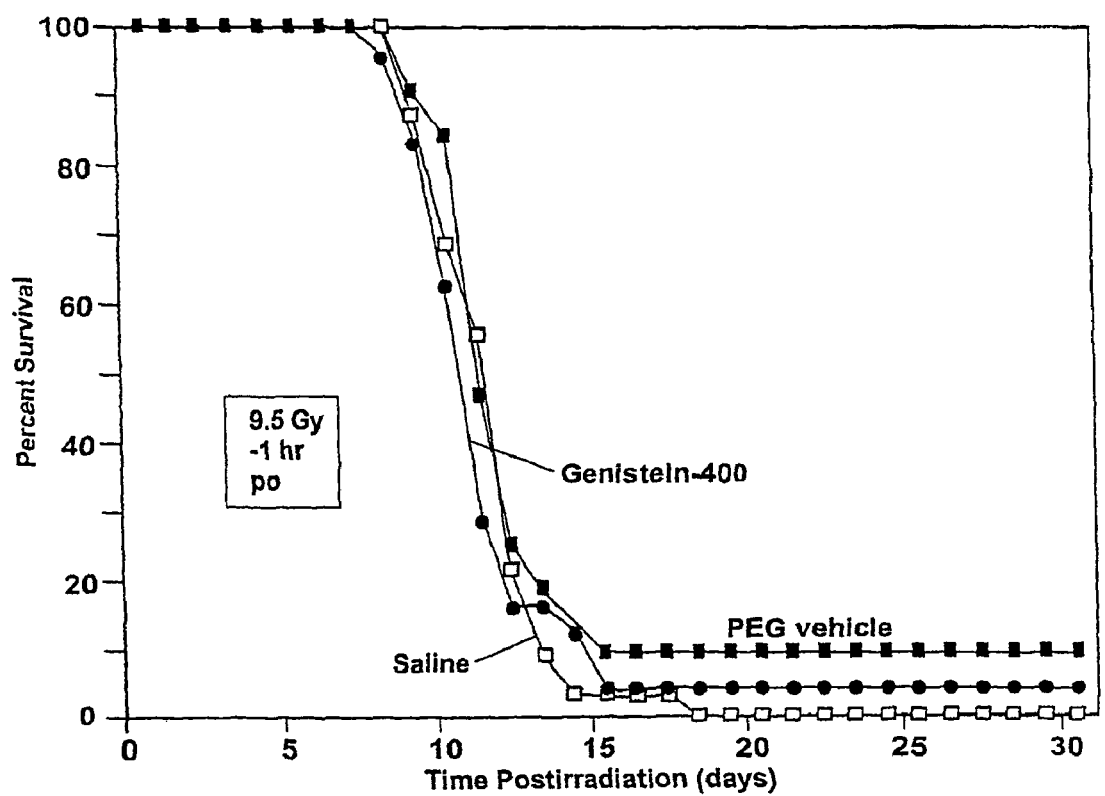
FIG. 7 shows the survival curve of mice administered a single oral (po) administration of saline, polyethylene glycol (PEG) vehicle, or 400 mg/kg genistein 1 hour before 9.5 Gy gamma radiation (N=24-32/group). Survival was monitored for 30 days postirradiation. This figure depicts the survival curve for the data illustrated in FIG. 6.
Figure 8:
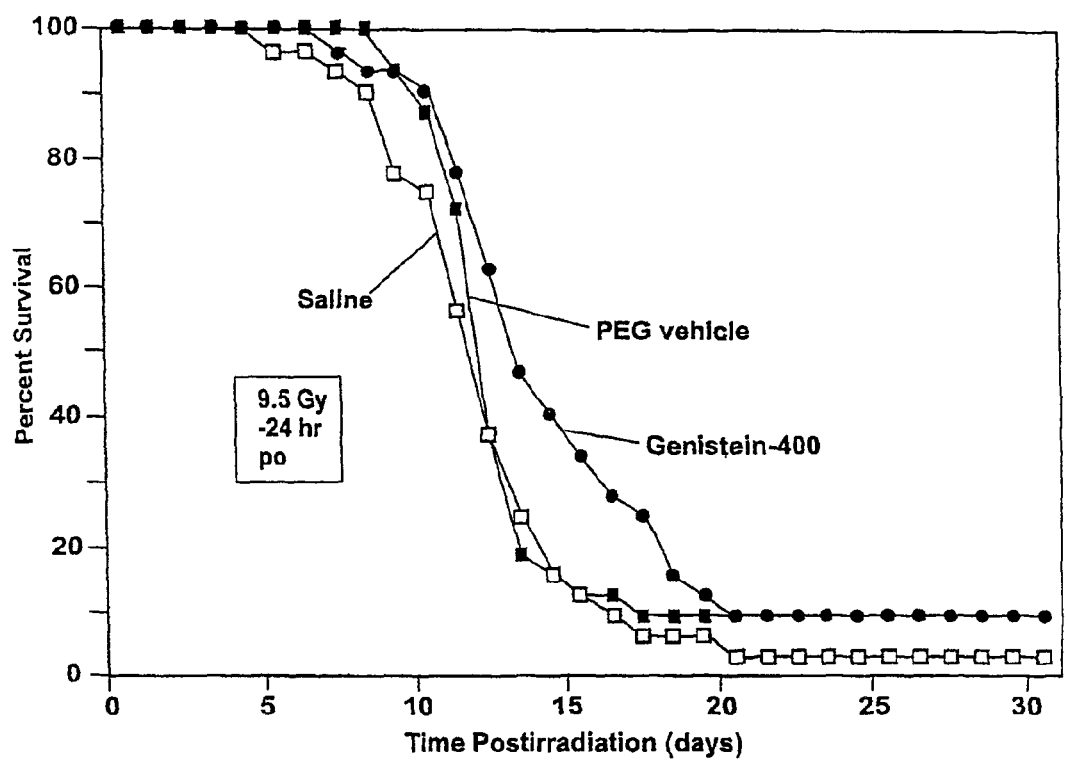
FIG. 8 shows the 30-day survival curve for mice administered a single oral (po) dose of saline, polyethylene glycol (PEG) vehicle, or 400 mg/kg genistein 24 hours before 9.5 Gy gamma radiation. Survival was monitored for 30 days postirradiation (N=24-32/group). This Figure depicts the survival curve for the data illustrated in FIG. 6. Although genistein did not protect against lethality, the data indicate that genistein treated mice survived for about a week longer than control animals.

As shown in FIGS. 3 and 4, the results demonstrated genistein did not enhance survival when given 1 hour before 8.5 Gy radiation. However, when given 24 hours before 8.5 Gy radiation, 63% of saline and vehicle control mice survived 30 days after irradiation while 88% of mice receiving a single dose of genistein survived, as shown in FIGS. 3 and 5. These results indicate that genistein has radioprotective qualities at this dose of radiation. When a higher does of radiation (9.5 Gy) was administered genistein given 1 hour or 24 hours before irradiation did not enhance survival, as shown in FIGS. 6 through 8. However, the mice that received 400 mg/kg genistein 24 hours before radiation lived for about a week longer than control animals indicating a beneficial effect of genistein (See, FIG. 8). To determine if multiple oral doses of genistein given daily before or before and after radiation would enhance survival, another experiment was conducted, as described in Example 2, below.

Example 2

Protective Effect of Multiple Oral Doses of Genistein

This Example describes experiments to determine the protective effect of multiple oral doses of genistein administered before or before and after radiation. In these experiments, mice (N=16/group) received po 100 mg/kg or 400 mg/kg genistein for either 4 days before (pre), 4 days after (post), or 4 days before and 4 days after (pre+post) a lethal dose of gamma radiation (9.5 Gy) Animals in the pre-irradiation genistein groups received the PEG vehicle after irradiation, and the postirradiation genistein groups received the PEG vehicle before irradiation. Thus, all of the animals received eight daily oral gavage of either vehicle or genistein. The postirradiation dosing began 1 hour after irradiation. Two control groups that received either saline or PEG both before and after irradiation were also included. This resulted in a total of eight treatment conditions: 1) saline control; 2) PEG vehicle control; 3) genistein-100 pre; 4) genistein-100 post; 5) genistein-100 pre+post; 6) genistein-400 pre; 7) genistein-400 post; and 8) genistein-400 pre+post.

Figure 9:
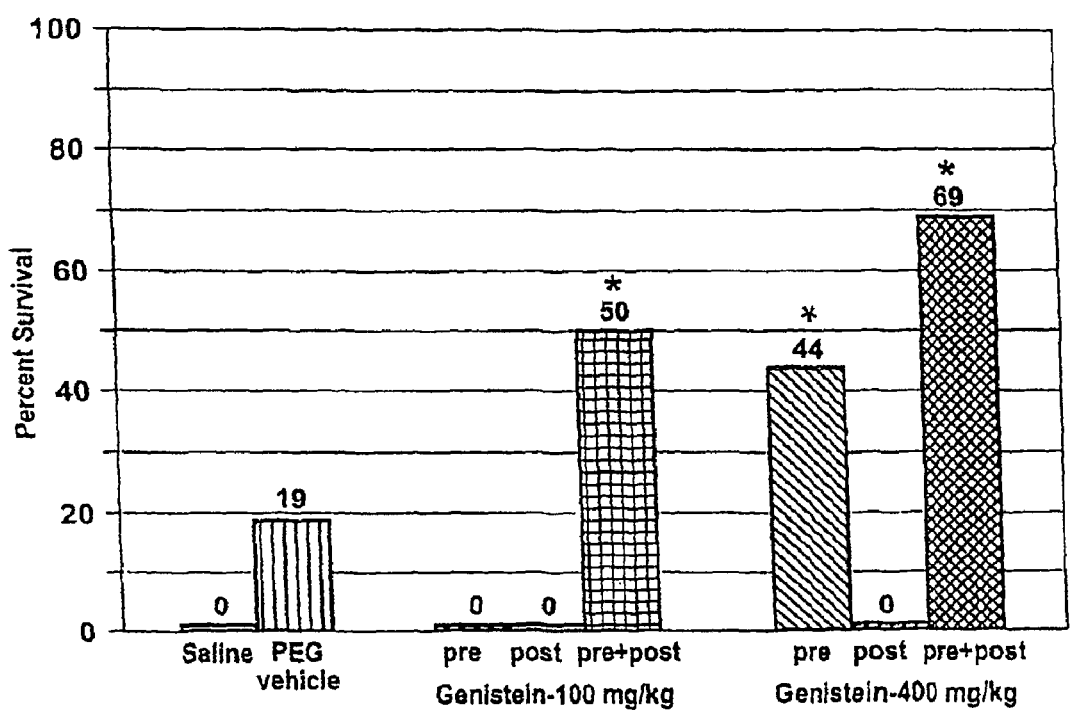
FIG. 9 shows a histogram of the percent survival of irradiated mice treated with multiple daily oral (po) treatment with saline, polyethylene glycol (PEG) vehicle, or genistein (100 mg/kg or 400 mg/kg) (N=16/group). Mice were either treated with genistein for 4 days before 9.5 Gy gamma radiation (pre), 4 days after 9.5 Gy radiation (pre), or 4 days before and 4 days after 9.5 Gy radiation (pre+post). Survival was monitored for 30 days. The asterisk indicates a significant difference from control.
Figure 10:
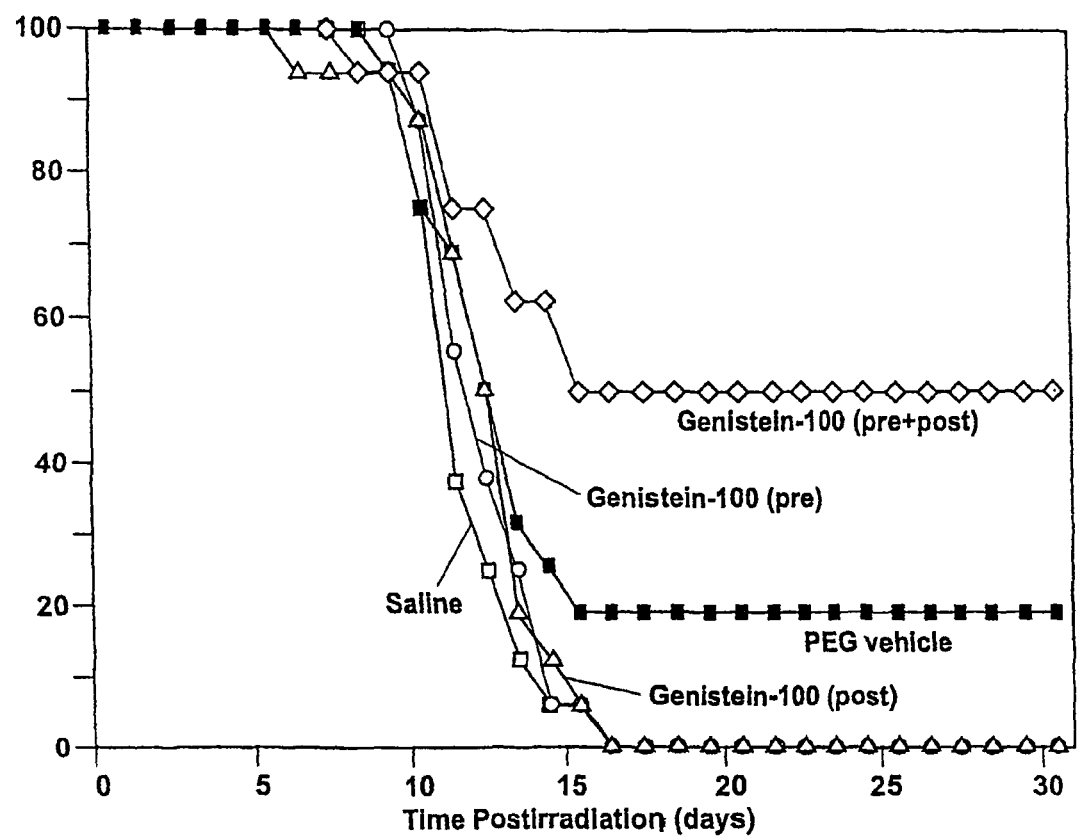
FIG. 10 shows the 30-day survival curve of mice treated with multiple daily oral (po) treatment with saline, polyethylene glycol (PEG) vehicle, or 100 mg/kg genistein (N=16/group). Mice were either treated with genistein for 4 days before 9.5 Gy gamma radiation (pre), 4 days after 9.5 Gy radiation (pre), or 4 days before and 4 days after 9.5 Gy radiation (pre+post). Survival was monitored for 30 days. This Figure depicts the survival curve for the data illustrated in FIG. 9.
Figure 11:
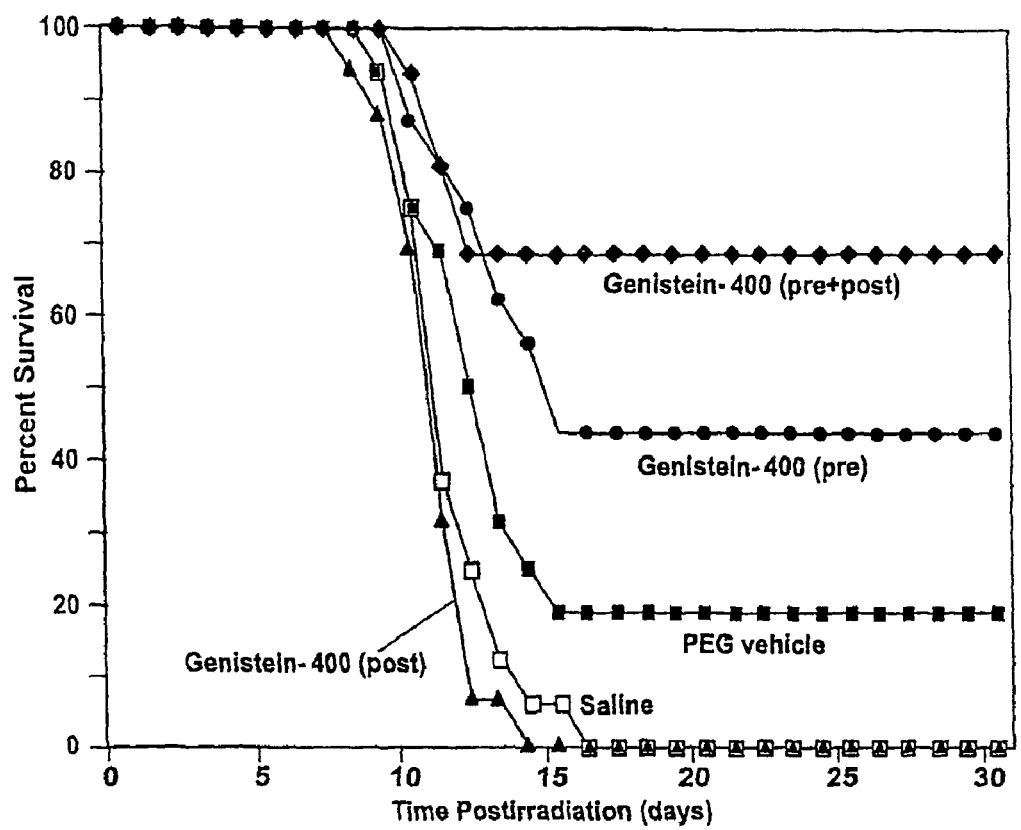
FIG. 11 shows the 30-day survival curve of mice treated with multiple daily oral (po) treatment with saline, polyethylene glycol (PEG) vehicle, or 400 mg/kg genistein. Mice were either treated with genistein for 4 days before 9.5 Gy gamma radiation (pre), 4 days after 9.5 Gy radiation (post), or 4 days before and 4 days after 9.5 Gy radiation (pre+post) (N=16/group). Survival was monitored for 30 days. This Figure depicts the survival curve for the data illustrated in FIG. 9.

The results indicated that multiple dosing of genistein are capable of protecting animals from radiation-induced lethality at relatively high doses (9.5 Gy) of gamma radiation. FIG. 9 provides the 30=day survival rates for saline, PEG vehicle, were only 0%, and 19%, respectively. As indicated in FIGS. 9 and 10, the survival rates for genistein-100 pre, post, and pre+post were 0%, 0% and 50%, respectively, while the survival rates for the genistein-400 pre, post, and pre+post groups were 44%, 0%, and 69%, respectively, as indicated in FIGS. 9 and 11. These experiments demonstrate that multiple oral doses of the isoflavone genistein are capable of protecting animals against a lethal dose of radiation.

Example 3

Subcutaneous Administration of Genistein

In this Example, experiments using another route of administration, namely a single subcutaneous injection of genistein administered 24 hours before radiation. In these experiments, mice received a single subcutaneous (so) injection in the nape of the neck with either saline, PEG vehicle, genistein 100 mg/kg, or genistein 400 mg/kg, 24 hours before a lethal dose of radiation. Both these doses of genistein were demonstrated to be nontoxic using the sensitive locomotor activity test, as described herein.

Figure 12:
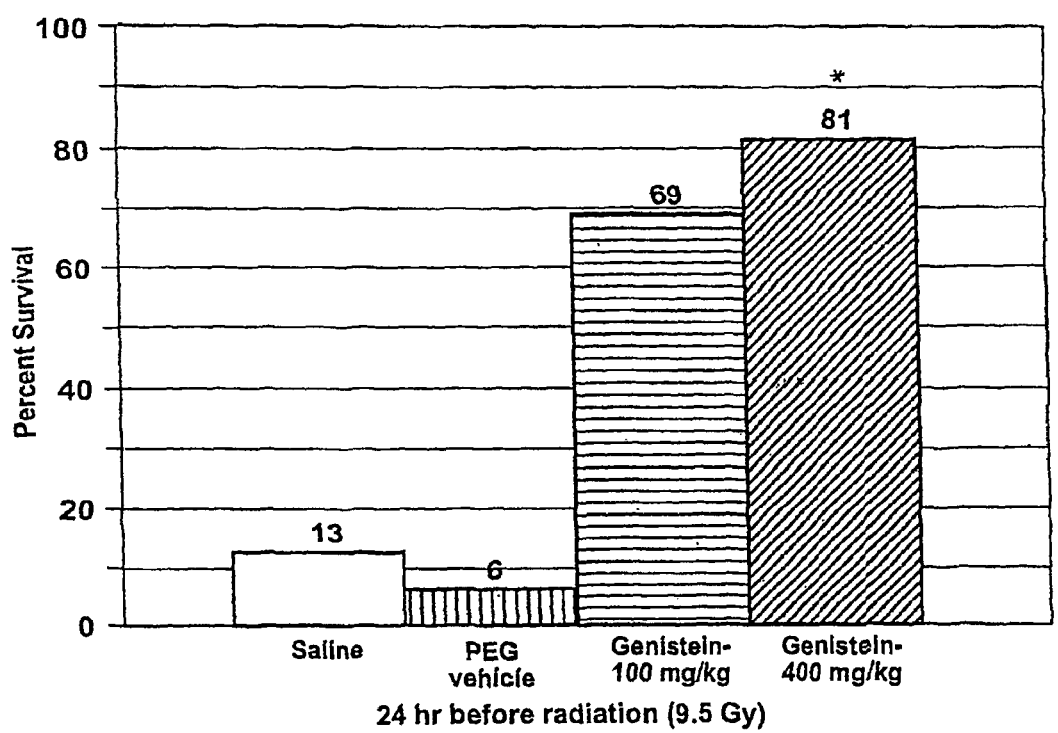
FIG. 12 shows the histogram for the effect of a single subcutaneous (sc) administration of genistein on 30-day survival of mice given genistein 24 hours before a 9.5 Gy dose of gamma radiation form a cobalt-60 source. The dose rate was 0.6 Gy/minute. Experimental groups consisted of saline, polyethylene glycol (PEG) vehicle, or genistein (100 mg/kg or 400 mg/kg) (N=16/group). A single dose of genistein administered at 100 or 400 mg/kg injected subcutaneously significantly protected mice from a lethal dose of gamma radiation. The asterisk indicates a significant difference from control.
Figure 13:
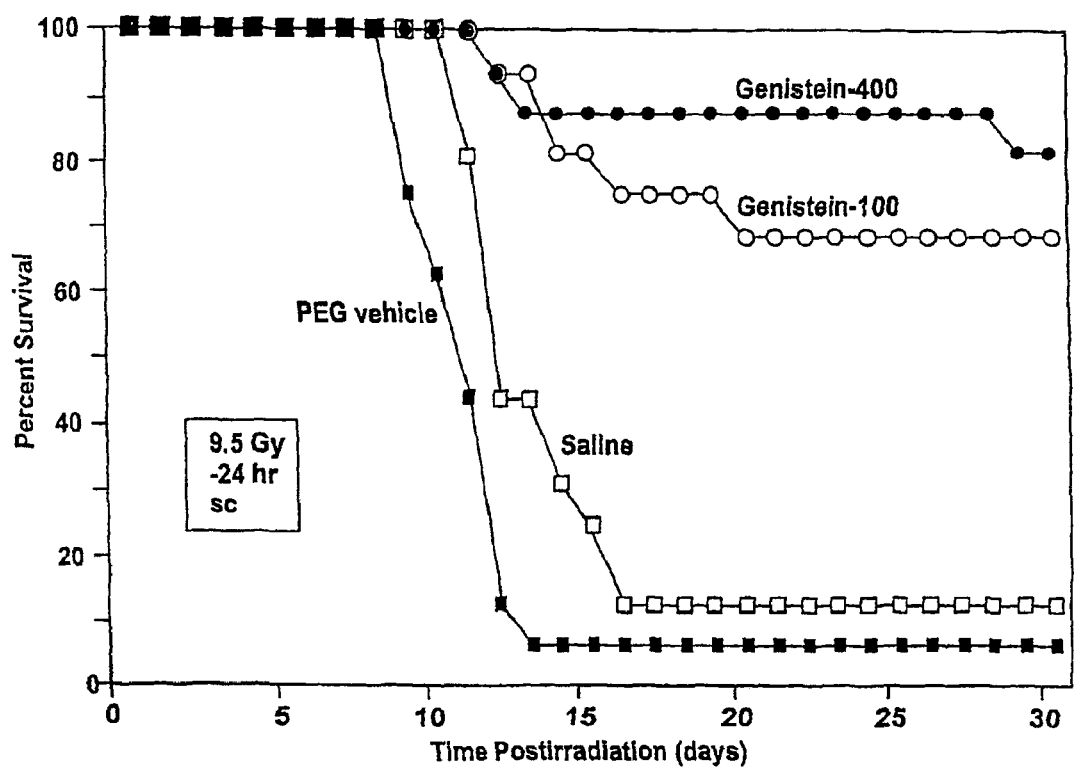
FIG. 13 shows the thirty-day survival curve for mice receiving a single subcutaneous (sc) injection of either saline, polyethylene glycol (PEG) vehicle, 100 mg/kg genistein or 400 mg/kg genistein, 24 hours before a 9.5 Gy dose of gamma radiation (N=16/group). This Figure depicts the survival curve for the data illustrated in FIG. 12.

Of the control mice that received saline or PEG vehicle, only 13% and 6%, respectively survived 30 days after total body radiation exposure. In contrast, significantly more mice survived in the groups that received a single dose of genistein, as indicated in FIGS. 12 and 13. Indeed, 69% of mice in the genistein-100 group survived, while 81% of those mice receiving genistein-400 survived. These results clearly demonstrate that a single dose of genistein administered subcutaneously is a very potent radioprotective agent.

Example 4

Behavioral Toxicity

In this Example, experiments conducted to determine the behavioral toxicity of a single oral dose of genistein that has been determined to be radioprotective are described. Behavioral experiments were conducted in non-irradiated mice to determine the effects of genistein on locomotor activity, a sensitive index of behavioral toxicity that is well-known in the art (MacPhail, J. Am. Coll. Toxicol., 8:117-125 [1989]).

In these experiments, computerized digiscan activity monitors (Omnitech) were used to quantify locomotor activity as previously described (Landauer et al., J. Radiat. Res., 38:45-54 [1997]). Each monitor used an array of infrared photodetectors spaced 2.5 cm apart to determine the total distance traveled. Immediately after an oral gavage (po) of saline, PEG vehicle, or 50, 100, 200 or 400 mg/kg genistein, the mice (N=8/group) were each placed into an individual Plexiglas activity chamber (20 cm×20 cm×30 cm). Locomotor activity testing commenced at the beginning of the dark cycle and continued for 48 hrs. Each animal was tested only once. Food and water were available throughout the testing period. No animals used in the behavioral studies were irradiated. An analysis of variance was used to statistically analyze locomotor activity data.

Figure 14:
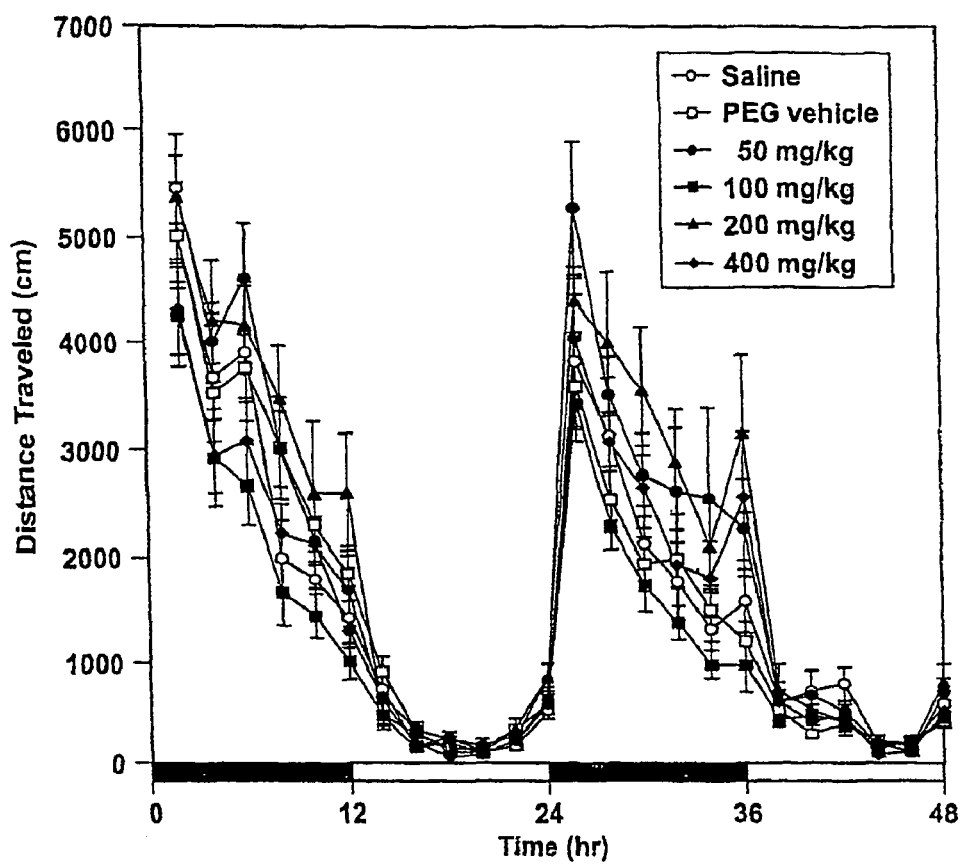
FIG. 14 shows the effects of a single oral (po) administration of saline, polyethylene glycol (PEG) vehicle, or genistein on locomotor behavior of mice over 48 hrs. Locomotor activity is expressed as the total distance traveled. The solid bars on the abscissa represent the dark period and the open bars the daylight period of the 12:12 hour light/dark cycle. Each mouse received a single oral gavage (per os, po) of saline, PEG vehicle, or 50, 100, 200, or 400 mg/kg genistein immediately before testing at the beginning of the dark period on the first day (N=8/group). Vertical lines represent the SEM. There were no significant differences among groups on locomotor activity, indicating that orally Administered genistein is nontoxic using this sensitive behavioral assay.

The behavioral studies revealed that all doses of genistein (50-400 mg/kg) administered orally by gavage (po) or subcutaneously by injection, had no effect on locomotor activity, as shown in FIG. 14. The behavior of the genistein treated animals were no different than the control groups, indicating that genistein has no motor side effects as indicated by this sensitive behavioral test.

Example 5

Behavioral Toxicity of Subcutaneous Genistein Injection

In this Example, experiments to determine whether a single subcutaneous injection of genistein has any behavioral side effects, as measured by the locomotor activity test of Example 4 are described.

Figure 15:
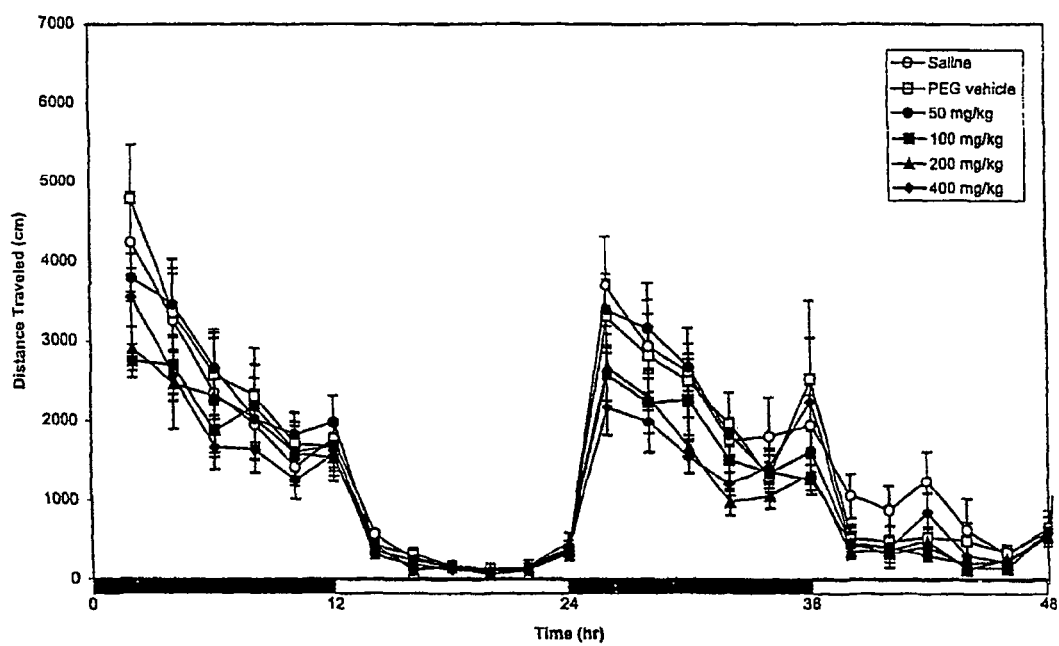
FIG. 15 shows the effects of a single subcutaneous (so) administration of saline, polyethylene glycol (PEG) vehicle, or genistein on Locomotor behavior of mice over 48 hrs. Locomotor activity is expressed as the total distance traveled. The solid bars on the abscissa represent the dark period and the open bars the daylight period of the 12:12 hour light/dark cycle. Each mouse received a single subcutaneous dose of saline, PEG vehicle, or 50, 100, 200, or 40D mg/kg genistein immediately before testing at the beginning of the dark period on the first day (N=8/group). Vertical lines represent the SEM. There were no significant differences among groups on locomotor activity indicating that subcutaneously administered genistein is nontoxic using this sensitive behavioral assay.

Immediately after receiving a subcutaneous (so) administration of saline, PEG vehicle, or 50, 100, 200 or 400 mg/kg genistein, the mice (N=8/group) were each placed into locomotor activity monitors as described above for 48 hours. The results indicate that sc administration of genistein had no effect on locomotor activity indicating that genistein did not result in behavioral toxicity, as shown in FIG. 15.

Example 6

Behavioral Toxicity Measured by the Grip Strength and Motor Coordination Tests

In this Example, experiments conducted to determine whether a single oral or subcutaneous injection of genistein produces behavioral toxicity as measured by the grip strength test or a motor coordination test are described. As discussed further below, these results further demonstrate the absence of toxicity at doses of 100, 200, or 400 mg/kg administered acutely either orally or subcutaneously.

I. Behavioral Experiments

Behavioral experiments were conducted using 10 groups of non-irradiated mice (N=10/group) to determine the acute effects of genistein on forelimb grip strength and motor coordination, using the inverted screen test. Each mouse, by group, received a single subcutaneous injection or single gavage of saline, PEG, or 100, 200, or 400 mg/kg of genistein. All drugs were administered subcutaneously with an injection volume of 0.1 ml. The day of injection was considered to be "day 0."

II. Grip-Strength Test

Forelimb grip strength performance was assessed using an established procedure (Meyer et al., Neurobehav. Toxicol; 1:233-236 [1979]). Peak forelimb grip strength was measured in kilograms by a Chatillon Digital Force Gauge (Model DFI2). The gauge was attached to a stainless steel T-bar. A mouse was placed with its forepaws on the T-bar and gently pulled backward by the tail at a steady rate until its grip was broken. In order to eliminate bias, the individual administering the grip strength test was unaware of the treatment received by the animal. Two trials per mouse were conducted and the average of these trials was computed to estimate forelimb grip strength. The tests were conducted on days 1, 4, and 14 after genistein administration during the light portion of the light/dark cycle.

Figure 16:
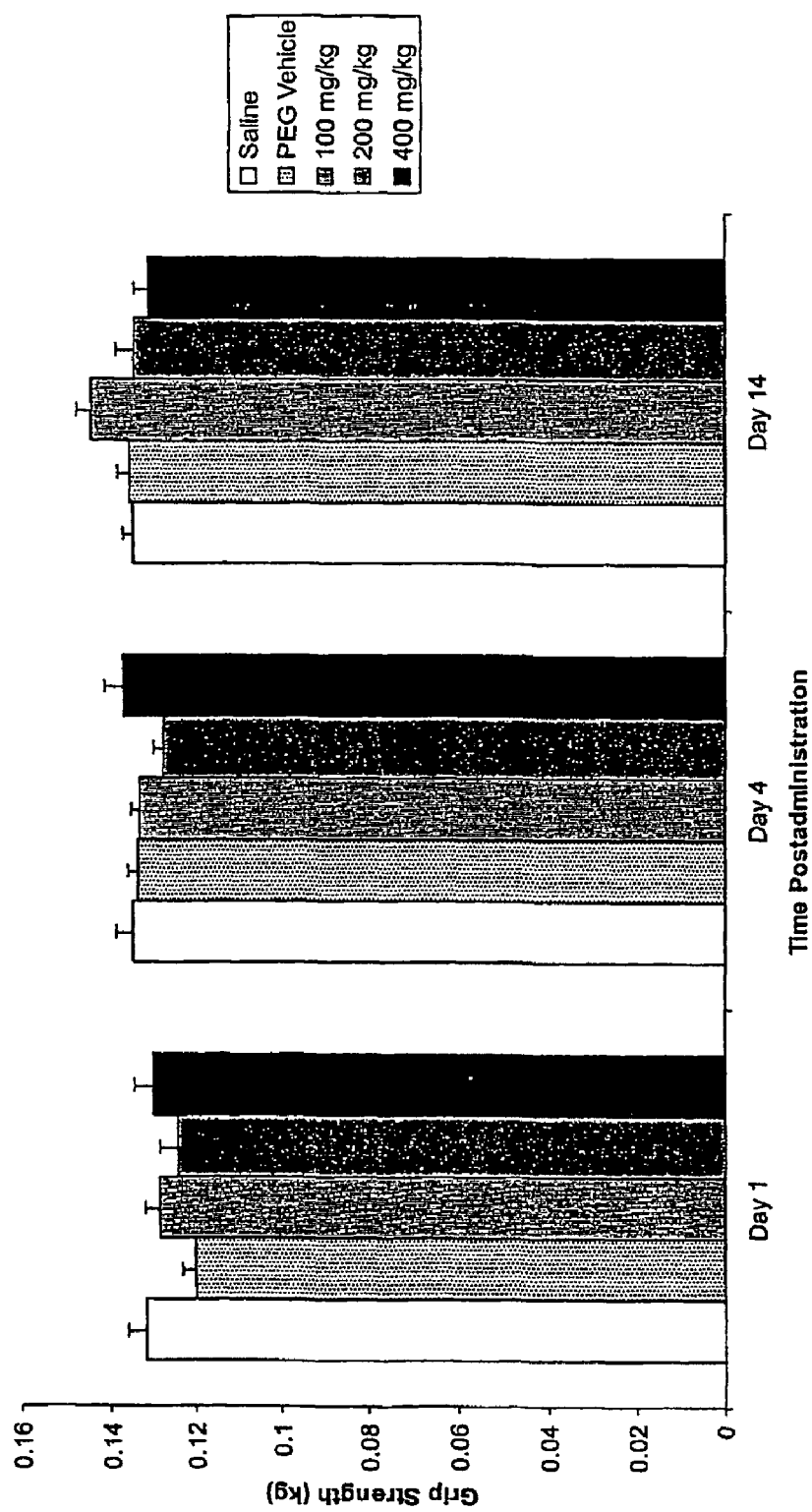
FIG. 16 shows the effect of genistein on forelimb grip strength for mice evaluated on days 1, 4 and 14 after acute subcutaneous administration of saline, PEG vehicle, or 100, 200, or 400 mg/kg of genistein. Day 0 was the day of injection. As indicated, there were no significant differences among groups.

FIG. 16 shows the effect of genistein on forelimb grip strength for mice evaluated on days 1, 4 and 14 after acute subcutaneous, administration of saline, PEG vehicle, or 100, 200, or 400 mg/kg of genistein. Day 0 was the day of injection. As indicated, there were no significant differences among groups.

Figure 17:
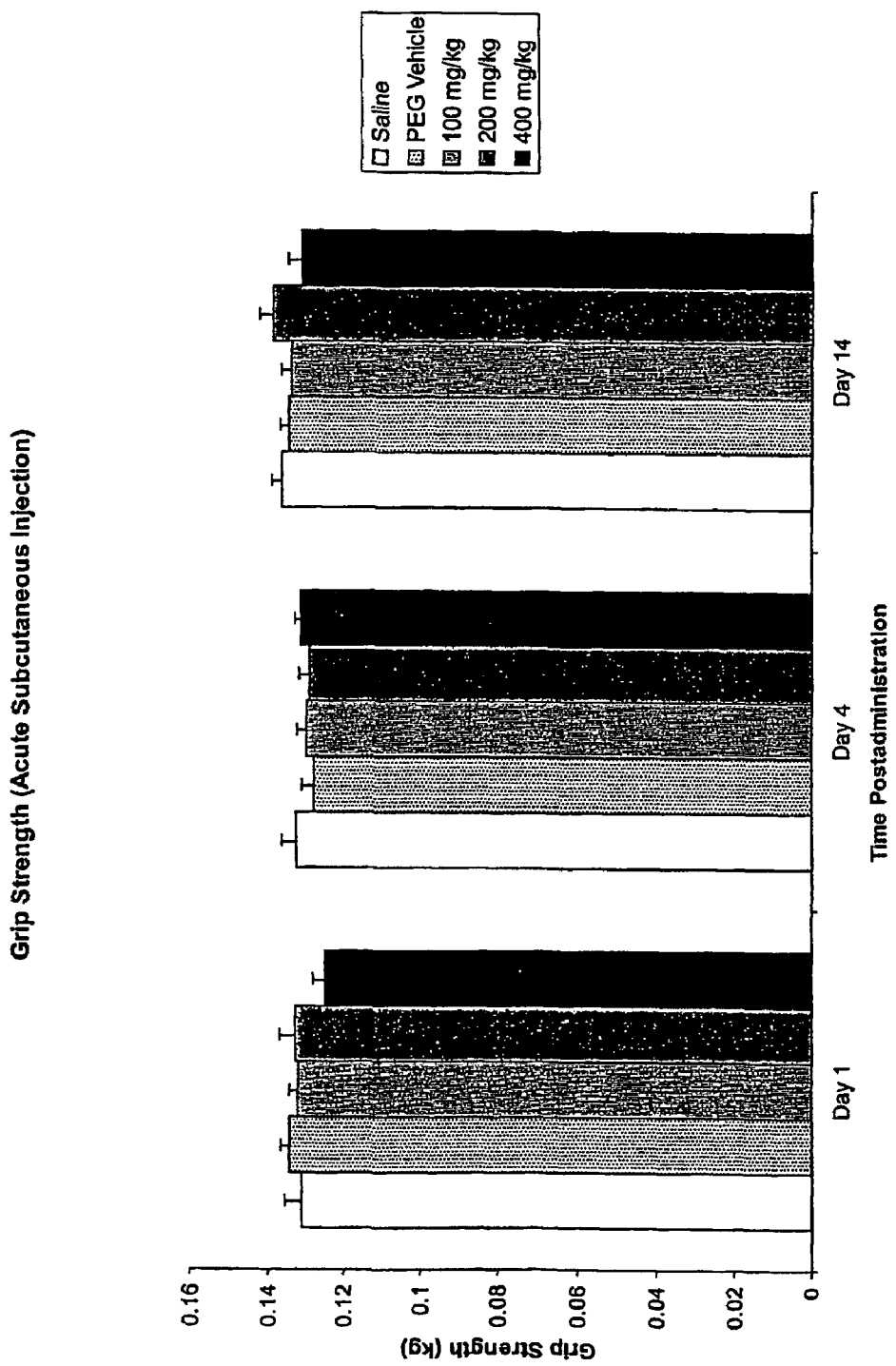
FIG. 17 shows the effect of genistein on forelimb grip strength for mice evaluated on days 1, 4 and 14 after acute oral gavage of saline, PEG vehicle, or 100, 200, or 400 mg/kg of genistein. Day 0 was the day of injection. There were no significant differences among groups.

FIG. 17 shows the effect of genistein on forelimb grip strength for mice evaluated on days 1, 4 and 14 after acute oral gavage of saline, PEG vehicle, or 100, 200, or 400 mg/kg of genistein. Day 0 was the day of injection. There were no significant differences among groups.

III. Motor Coordination Assessment

In addition to the grip strength test, motor coordination was assessed using the inverted screen test (Coughenour at al., Pharmacol. Biochem. Behav., 6:351-353 [1977]). Each mouse was placed alone on top of one of four wire mesh screens, each measuring 13×13 cm, that were mounted horizontally on a metal rod 31 cm above the tabletop. The apparatus was then slowly rotated 180 degrees so that the mouse was suspended upside down on the bottom of the screen. The natural tendency is for the mouse to climb on top of the screen. After 60 seconds, each animal was assigned to one of two groups: (1) animals that climbed to the top; and (2) animals that clung to the bottom or fell off the screen. An animal was considered to have passed the test if it was able to climb back on top of the screen with all four paws within 60 seconds. A cushion, placed beneath each screen to prevent injury to an animal should it fall, was at a sufficient height so that the mouse would not elect to drop. All mice were pretested 24 hours before treatment and only those capable of climbing to the top of the screen in the pretest were used in this experiment.

Figure 18:
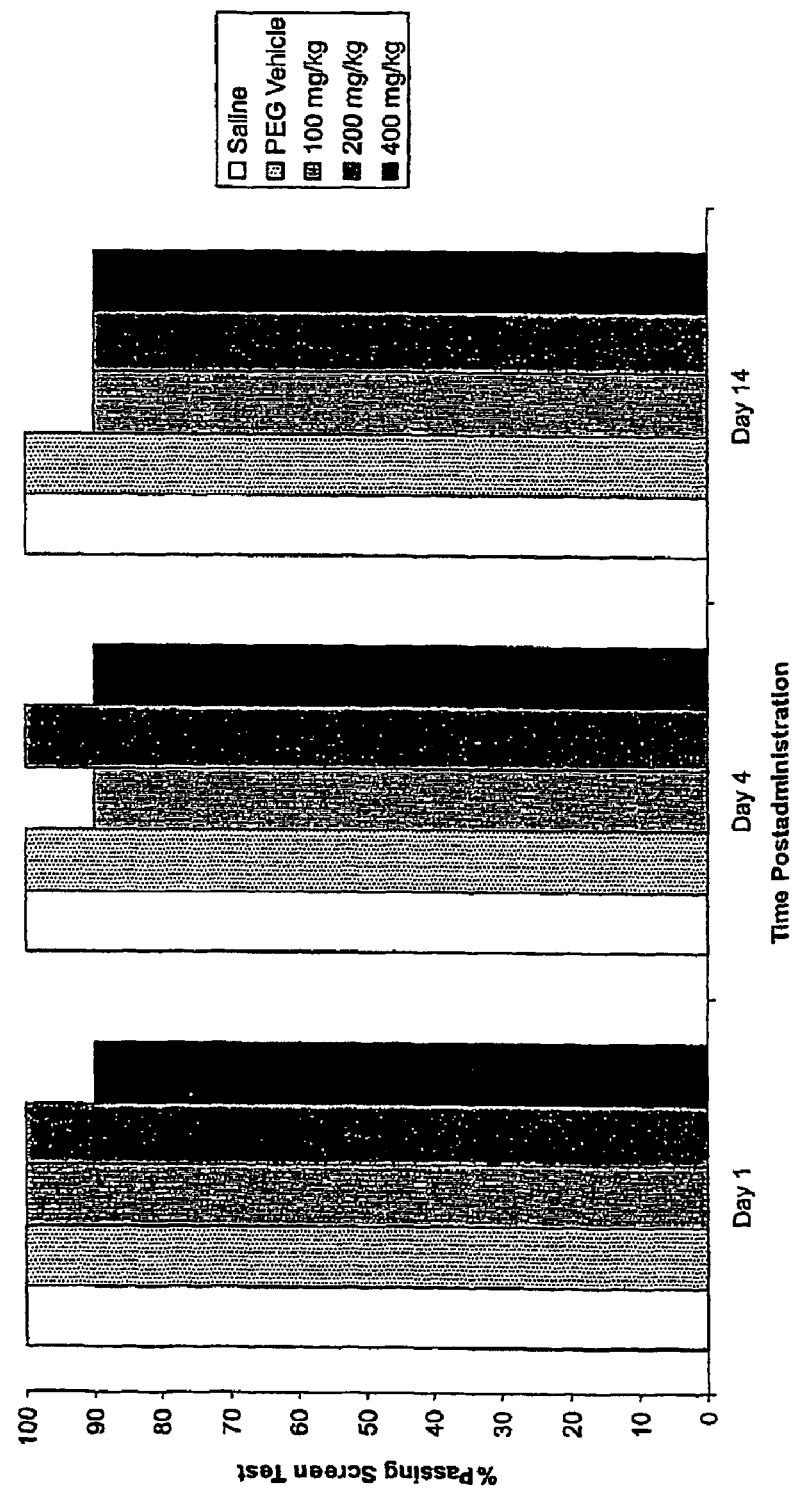
FIG. 18 shows the effect of genistein on motor coordination as measured by the inverted screen test for mice evaluated on days 1, 4, and 14 after acute subcutaneous administration of saline, PEG vehicle, or 100, 200, or 400 mg/kg of genistein. As indicated, there were no significant differences among groups.

FIG. 18 shows the effect of genistein on motor coordination as measured by the inverted screen test for mice evaluated on days 1, 4, and 14 after acute subcutaneous administration of saline, PEG vehicle, or 100, 200, or 400 mg/kg of genistein. As indicated, there were no significant differences among groups.

Figure 19:
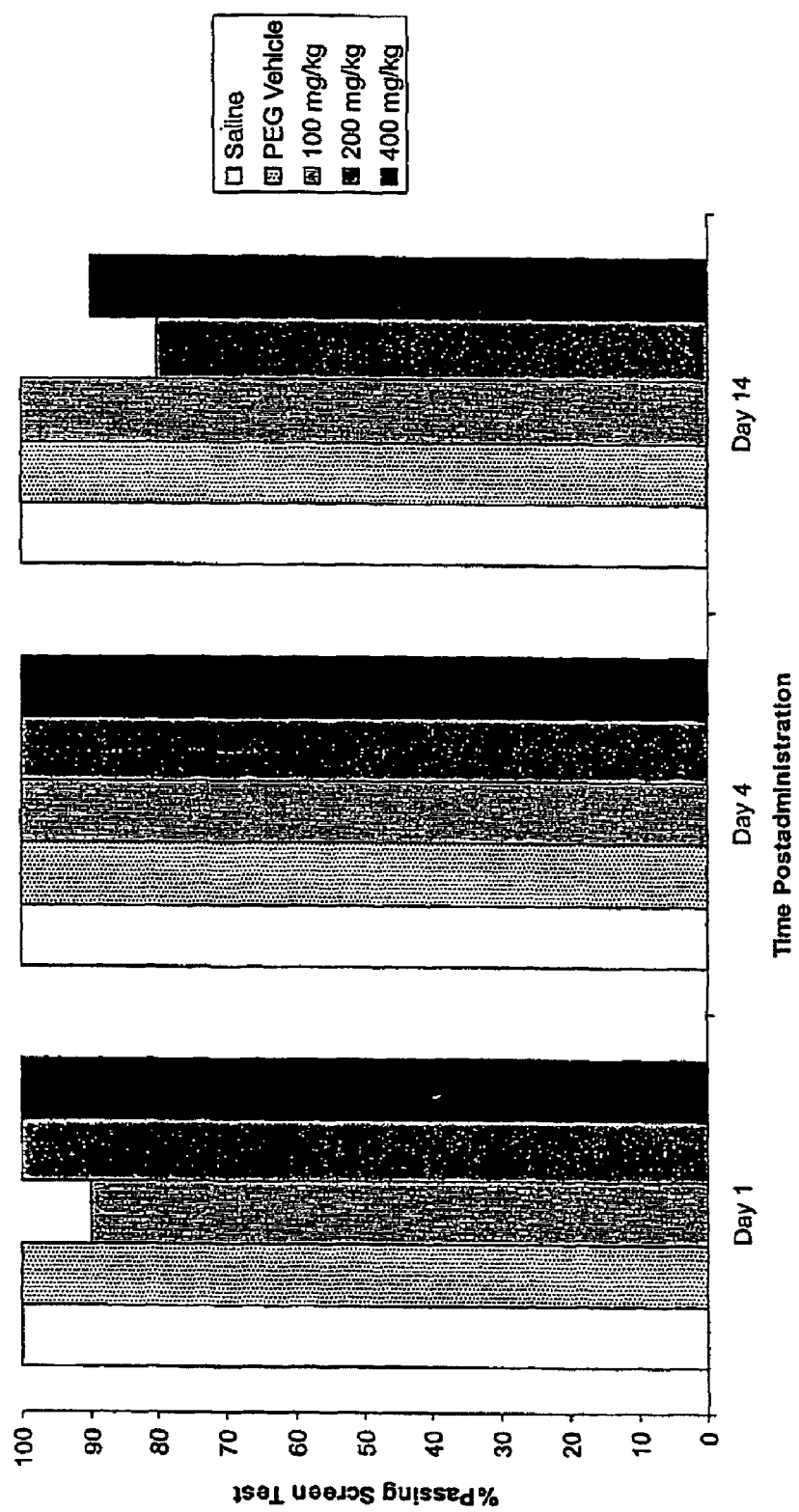
FIG. 19 shows the effect of genistein on the motor coordination using the inverted screen test for mice evaluated on days 1, 4, and 14 after acute oral administration of saline, PEG vehicle, or 100, 200, or 400 mg/kg of genistein. As indicated, there were no significant differences among groups.

FIG. 19 shows the effect of genistein on the motor coordination using the inverted screen test for mice evaluated on days 1, 4, and 14 after acute oral administration of saline, PEG vehicle, or 100, 200, or 400 mg/kg of genistein. As indicated, there were no significant differences among groups.

IV. Body Weight

The same non-irradiated animals used for the grip strength and inverted screen tests were weighed throughout the 14-day period following injection. Clinical signs such as lethargy, fur condition, and general well-being were monitored at the time of weighing.

Figure 20:
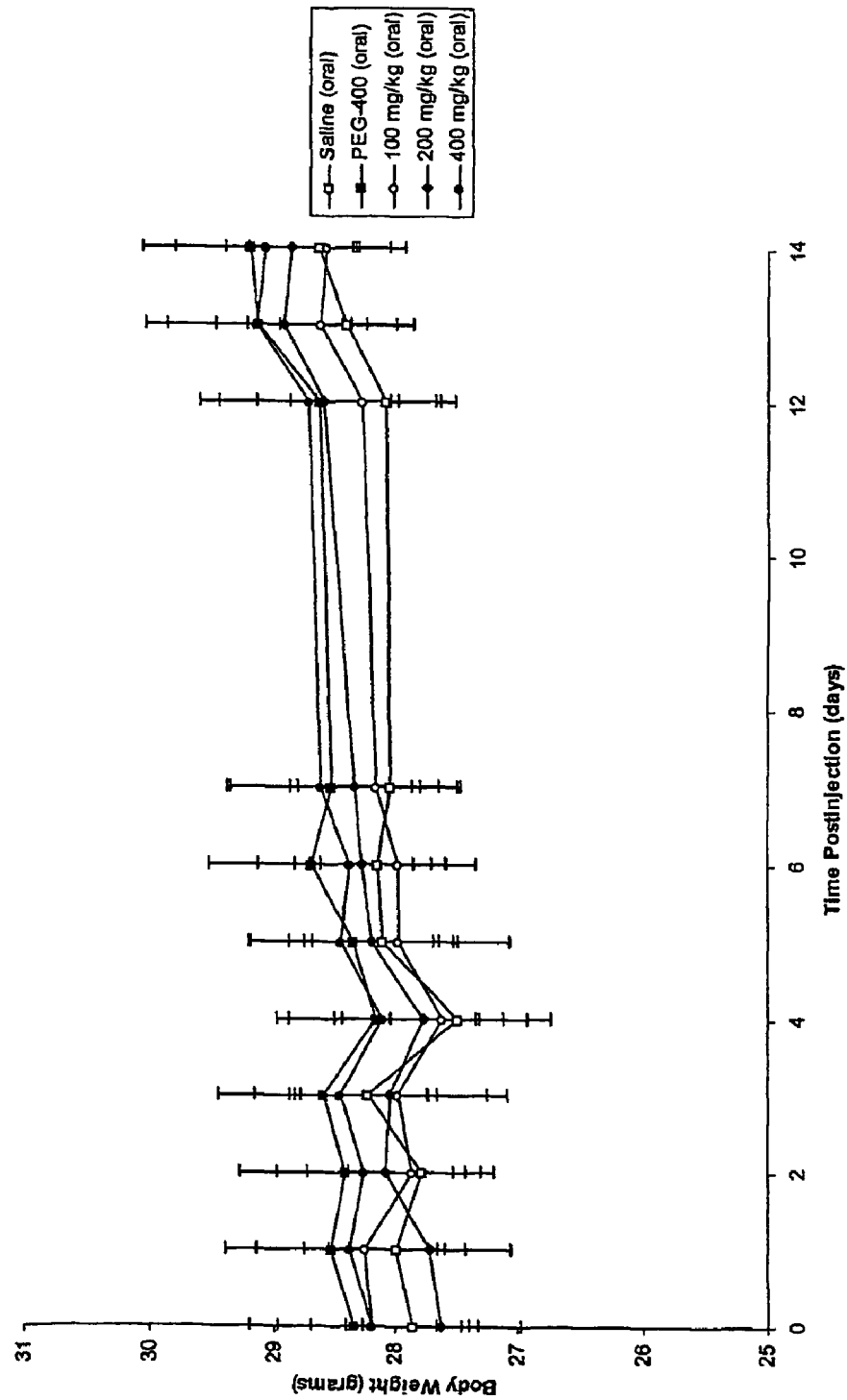
FIG. 20 shows the mean (SEM) body weight of mice administered an acute subcutaneous dose of saline, PEG vehicle, or 100, 200, or 400 mg/kg of genistein. As indicated, there were no significant differences among groups.

FIG. 20 shows the mean (SEM) body weight of mice administered an acute subcutaneous dose of saline, PEG vehicle, or 100, 200, or 400 mg/kg of genistein. As indicated, there were no significant differences among groups.

Figure 21:
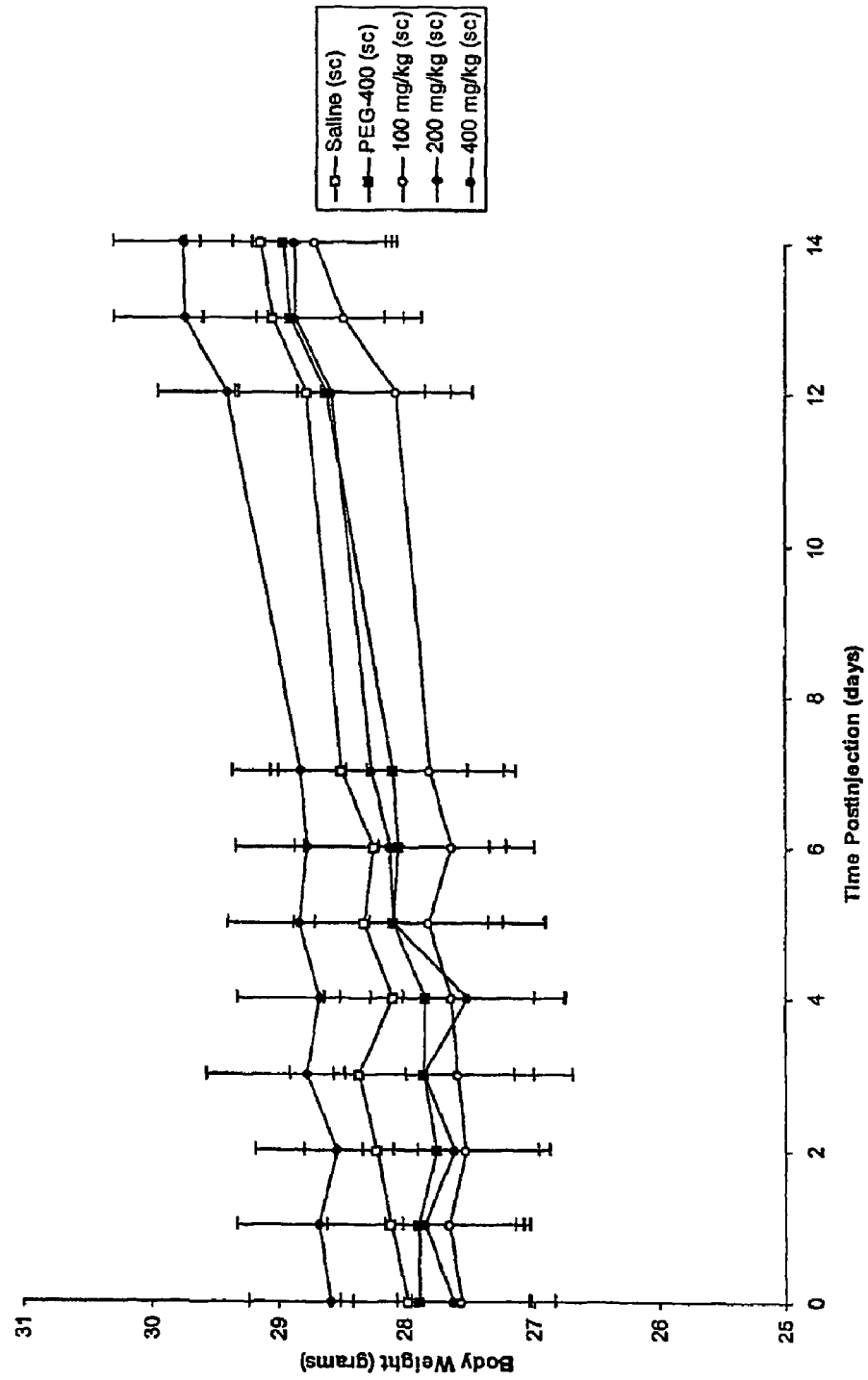
FIG. 21 shows the mean SEM body weight of mice administered an acute oral dose of saline, PEG vehicle, or 100, 200, or 400 mg/kg of genistein. As indicated, there were no significant differences among groups.

FIG. 21 shows the mean SEM body weight of mice administered an acute oral dose of saline, PEG vehicle, or 100, 200, or 400 mg/kg of genistein. As indicated, there were no significant differences among groups.

V. Testes Weights and Histopathology

On day 14 after injection, all mice from the two control groups (saline and PEG) and those from the high-dose group (400-mg/kg genistein) were euthanized and necropsied. Following the gross examination of each animal, tissues from the testes, liver, adrenal gland, mesenteric lymph node, spleen, and bone marrow of the femur and sternum were collected, fixed in buffered formalin, paraffin embedded, sectioned, and stained by hematoxylin and eosin using methods known in the art. The wet weight of both testes without epididymes was determined before fixing in formalin. A board-certified veterinerary pathologist examined all tissues. The results indicated that all gross necropsies and histopathology were normal.

Figure 22:
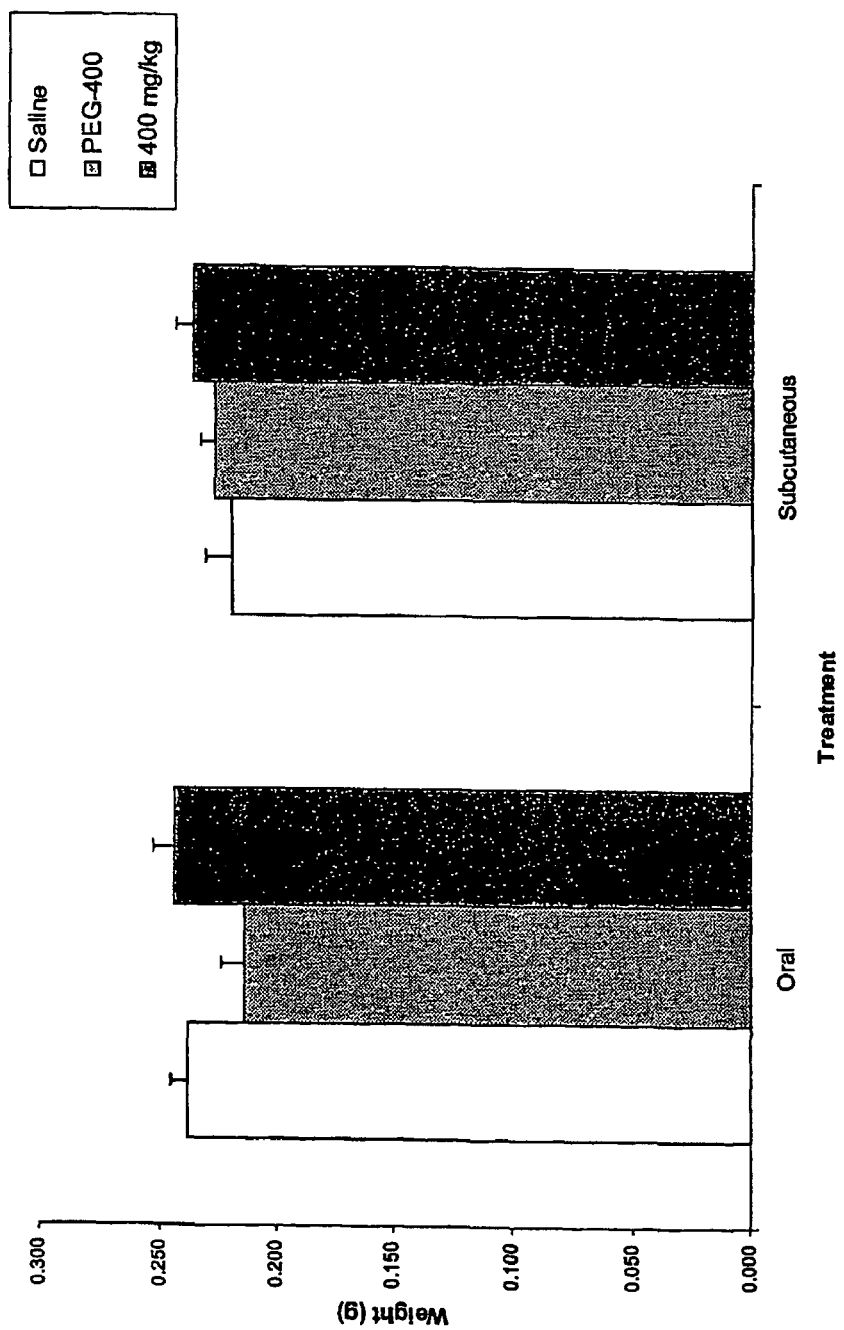
FIG. 22 shows the effect of a single oral gavage or subcutaneous injection of saline, PEG vehicle, or 400 mg/kg of genistein on testes weights. Weights reflect the sum, 14 days after injection, of both testes with epididymes removed. Vertical lines represent the mean " SEM. As indicated, there were no significant differences among groups.

FIG. 22 shows the effect of a single oral gavage or subcutaneous injection of saline, PEG vehicle, or 400 mg/kg of genistein on testes weights. Weights reflect the sum, 14 days after injection, of both testes with epididymes removed. Vertical lines represent the mean " SEM. As indicated, there were no significant differences among groups.

VI. Statistical Analysis

An analysis of variance and the Fisher's Least Significant Difference test was used to statistically analyze grip strength, body weight, and testes weight. The Fisher's exact test was used for analysis of the inverted screen test and 30-day survival data.

The results indicated that acute oral or subcutaneous doses (100-, 200-, 400-mg/kg) of the soy isoflavone genistein administered to non-irradiated adult male mice resulted in no adverse clinical signs or behavioral toxicity. Acute oral or subcutaneous doses of 100-400 mg/kg of genistein resulted in no changes in body weight. There were no effects from PEG vehicle or 400 mg/kg (high dose) of genistein on testes weights after an acute oral or subcutaneous administration of genistein when compared with the testes weights for the saline control group. The gross necropsy and pathological examination of adult mice treated with 400 mg/kg of genistein or PEG vehicle revealed no abnormalities in tissue morphology.

Example 7

Determination of Optimal Subcutaneous Protective Dose

In this Example, experiments conducted to determine the optimal dose and the range of doses wherein a single subcutaneous dose of genistein administered 24 hours before radiation exposure protects mice against radiation injury, the following experiment are described. Radioprotection was measured by 30-day survival. A dose-response experiment was performed where the radiation dose was 9.5 Gy 60-Cobalt and the dose rate was 0.6 Gy/min. The radiation procedure used was the same as described above.

Figure 23:
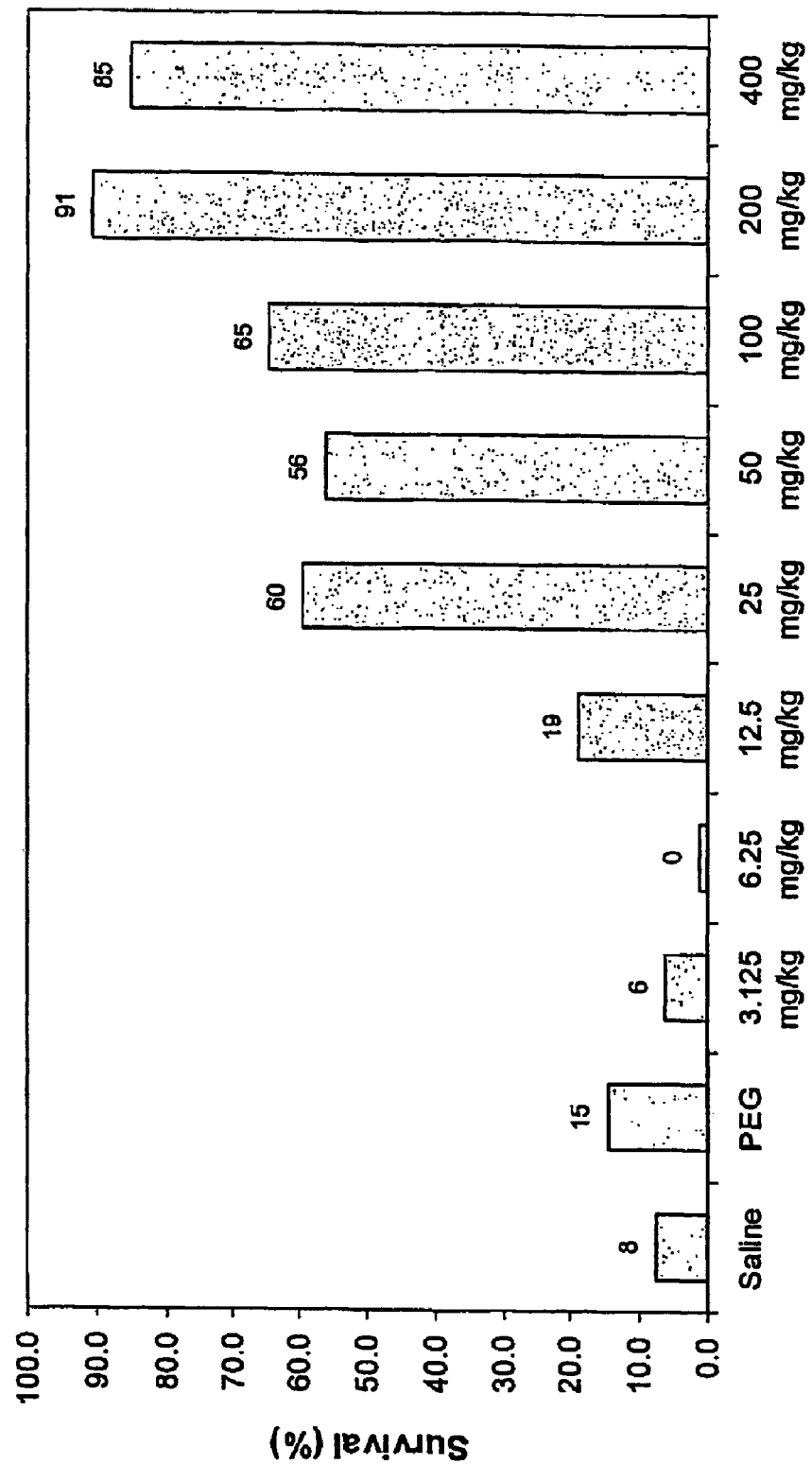
FIG. 23 provides a histogram showing the effect of a single subcutaneous dose of genistein on 30-day survival. Genistein (3.125-400 mg/kg) was administered 24 hr before 9.5 Gy radiation at a dose rate of 0.6/Gy minute.
Figure 24:
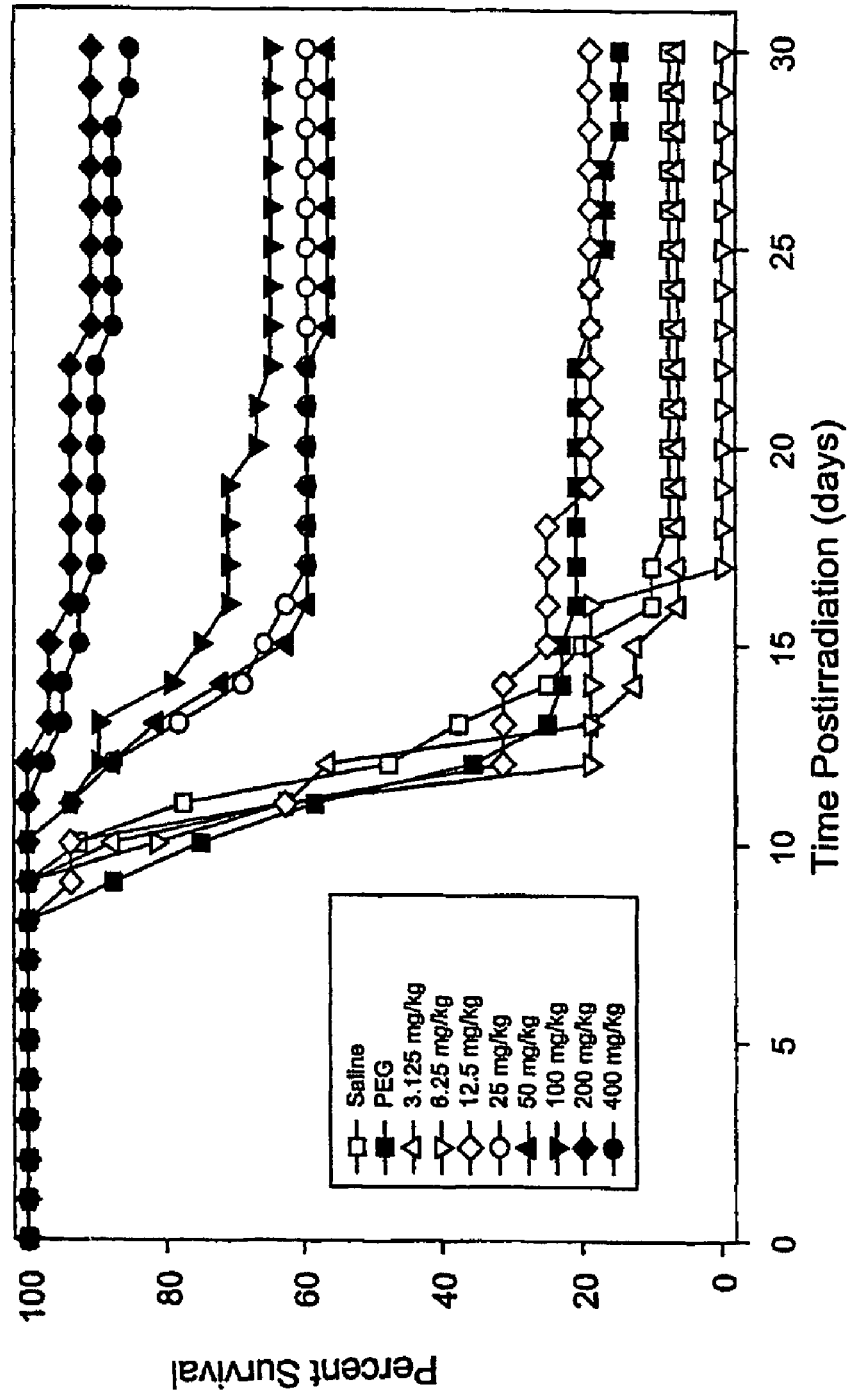
FIG. 24 provides a 30-day survival curve for mice given a single subcutaneous injection of genistein. Mice received doses of 3.125-400 mg/kg 24 hours before 9.5 Gy cobalt-60 irradiation. Significantly more mice survived 30 days after lethal dose of radiation if they had received 25 to 400 mg/kg of genistein 24 hours before radiation exposure.

In these experiments, male CD2F1 mice (N=16-48/group) were administered a single subcutaneous dose of genistein in PEG-400 vehicle. Each mouse received either saline, PEG-vehicle, 3.12, 6.25, 12.5, 25, 50, 100, 200 or 400 mg/kg genistein administered subcutaneously 24 hr before 9.5 Gy at 0.6 Gy/min. The percent surviving for each of these group after 30 days was: saline=8%, PEG-400 vehicle=15%, 3.125 mg/kg genistein=6%, 6.25 mg/kg=0%, 12.5 mg/kg=19%, 25 mg/kg=60%, 50 mg/kg=56%, 100 mg/kg=65%, 200 mg/kg=91%, and 400 mg/kg=85%, as shown in FIGS. 23 and 24. These data demonstrate that doses of 25 mg/kg genistein or higher are significantly ($p<0.001$) better than vehicle in protecting mice from radiation injury.

In summary, the present invention provides numerous advances and advantages over the prior art, including methods and compositions for the radioprotection. All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in diagnostics, cell culture, and/or related fields are intended to be within the scope of the following claims.

We claim:

1. A method of enhancing the 30 day survival of an animal exposed to an acute, lethal dose of ionizing radiation comprising administering to the animal a therapeutically effective amount of natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof.

2. The method of claim 1 wherein the dose of ionizing radiation normally produces lethality in said animal within a time period less than a year.

3. The method of claim 1 wherein the administration is made prior to the exposure.

4. The method of claim 1 wherein the administration is made 10 minutes to 96 hours subsequent to commencement of the exposure.

5. The method of claim 1 wherein the administration is made after the exposure.

6. The method of claim 1 wherein the administration is made from about 1 minute to 48 hours after radiation exposure.

7. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is dissolved in a vehicle.

8. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is part of a composition further comprising one or more pharmaceutically acceptable carriers, excipients, auxiliaries, and diluents.

9. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is systemically administered.

10. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is administered to said animal in a single dose.

11. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is administered to said animal in multiple doses.

12. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is contained in one or more pills, capsules, liquids, gels, powders, suppositories, suspensions, creams, jellies, aerosol sprays, or dietary supplements.

13. The method of claim 12, wherein said dietary supplement comprises an unprocessed soy food.

14. The method of claim 12, wherein said dietary supplement comprises isolated soy protein.

15. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is utilized in amount of from about 0.1 mg to about 2000 mg.

16. The method of claim 1, wherein said the dosage of said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof administered to said animal comprises from about 30 mg/day to about 200 mg/day of said isoflavonoid.

17. The method of claim 1, wherein said natural or synthetic genistein, 6"-O-Mal genistein, 6"-O—Ac genistein, daidzein, 6"-O' Mal daidzein, 6"-O—Ac daidzein, glycitein, glycitin, 6"-O-Mal glycitin, biochannin A, formononetin, or derivatives, analogs, or mixtures thereof is administered to said animal is in a dosage of an effective amount less than about 400 mg/kg/day of the body weight of said animal.

18. The method of claim 1, wherein said administering is subcutaneous injection, oral administration, intravenous administration, rectal administration, vaginal administration, topical administration, intramuscular administration, intranasal administration, transdermal administration, subconjunctival administration, intraocular administration, periocular administration, retrobulbar administration, subretinal, suprachoroidal administration, or intrathecal administration.

19. The method of claim 1, wherein said administering is administration from mechanical reservoirs, devices, implants, or patches.

20. The method of claim 1, wherein said radiation is ionizing radiation, alpha radiation, beta radiation, gamma radiation, or neutrons.

* * * * *

UNITED STATES PATENT AND TRADEMARK OFFICE
CERTIFICATE OF CORRECTION

PATENT NO. : 8,349,888 B2  
APPLICATION NO. : 12/696285  
DATED : January 8, 2013  
INVENTOR(S) : Michael R. Landauer et al.

Page 1 of 1

It is certified that error appears in the above-identified patent and that said Letters Patent is hereby corrected as shown below:

On the Title Page,

Item [73] Assignees:

Delete "Washington, DC (US);" and insert -- Rockville, MD (US); --.

Signed and Sealed this  
Eighteenth Day of June, 2013

Teresa Stanek Rea  
*Acting Director of the United States Patent and Trademark Office*